United States Patent [19]

Marcker et al.

[11] Patent Number: 4,886,753

[45] Date of Patent: Dec. 12, 1989

[54] METHOD FOR THE EXPRESSION OF GENES IN PLANTS, PARTS OF PLANTS, AND PLANT CELL CULTURES, AND DNA FRAGMENTS, PLASMIDS, AND TRANSFORMED MICROORGANISMS TO BE USED WHEN CARRYING OUT THE METHOD, AS WELL AS THE USE THEREOF FOR THE EXPRESSION OF GENES IN PLANTS,

[75] Inventors: Kjeld A. Marcker, Egå ; Jens S. Jensen, Århus, both of

[73] Assignee: A/S De Danske Sukkerfabrikker, Copenhagen, Denmark

[21] Appl. No.: 858,924

[22] Filed: May 2, 1986

[30] Foreign Application Priority Data

Jan. 28, 1986 [DK] Denmark ............................ 412/86

[51] Int. Cl.$^4$ ................................................ C12N 15/00
[52] U.S. Cl. .................................. 435/172.3; 435/320; 935/35; 935/41; 935/43; 935/67
[58] Field of Search ................... 435/172.3, 240, 253, 435/317, 240.4, 320; 536/27; 800/1

[56] References Cited

PUBLICATIONS

Chemical Abstracts, vol. 101, 1984, p. 372, No. 107544m, by A. Marcker et al.; "Transcription of the Soybean Leghemoglobin Genes During Nodule Development".

Chemical Abstracts, vol. 104, 1986, p. 149, No. 103201m, K. Bojsen et al.; "Structure and transcription of the Soybean Leghemoglobin and Nodulin Genes".

Nature, vol. 321, 12th Jun. 1986, pp. 669–674, by J. S. Jensen et al.; "Nodule-Specific Expression of a Chimaeric Soybean Leghaemoglobin Gene in Transgenic *Lotus corniculates*".

Biological Abstracts/RRM, No. 31093068, Biological Abstracts, Inc., J. Schell; "Regulated Gene Expression in Transgenic Plants", Mar.-Apr. 30, 1986, J. Cell Biochem., 1986, vol. 0, No. 10 Part D, p. 75.

Nature, vol. 317, No. 6039, 24th Oct. 1985, pp. 741–744; by L. Comai et al.; "Expression in Plants of a Mutuant aroA Gene from *Salmonella typhimurium* Confers Tolerance to Glyphosate".

Chemical Abstracts, vol. 100, 1984, p. 131, No. 115743v, K. A. Marcker et al.; "The Structure and Organization of the Soybean Leghemoglobin Genes".

Chemical Abstracts, vol. 105, 1986, p. 192, No. 128581u, by J. Schell et al.; "Transfer and Regulation of Expression of Chimeric Genes in Plants", Cold Spring Harbor Symp. Quant. Biol. 1985.

Proc. Natl. Acad. Sci. U.S.A., vol. 79, Jul. 1982, pp. 4055–4059; N. Brisson et al.; "Soybean Leghemoglobin Gene Family: Normal, Pseudo, and Truncated Genes".

The EMBO Journal, vol. 4, No. 10, 1985, pp. 2431–2438, IRL Press Ltd., Oxford, GB., S. L. WOng et al.; "Promoter Analysis of a Soybean Nuclear Gene Coding for Nodulin-23, a Nodule-Specific Polypeptide Involved in Symbiosis with Rhizobium".

UCLA Symp. Mol. Cell. Biol. New. Ser., vol. 12, 1983, pp. 367–379, by Alan R. Liss, Inc.,; "The Soybean Leghemoglobin Gene Family".

Flick et al., pp. 29–33, In: Handbook of Plant Cell Culture, vol. 1, Evans et al., eds. MacMillan: New York 1984.

Facciotti et al., 1985, Biotechnol. 3(3): pp. 241–246.

Goodman et al., 1987, Science 236: pp. 48–54.

(List continued on next page.)

*Primary Examiner*—Charles F. Warren
*Assistant Examiner*—David T. Fox
*Attorney, Agent, or Firm*—Oblon, Spivak, McClelland, Maier & Neustadt

[57] ABSTRACT

A method for the expression of genes in plants, parts of plants, and plant cell cultures, in which a DNA fragment is used comprising an inducible plant promoter of root nodule-specific genes, DNA-fragments comprising an inducible plant promoter, to be used when carrying out the method, said DNA-fragments being identical with, derived from or comprising a 5' flanking region of root nodule-specific genes of any origin as well as plasmids and transformed *Agrobacterium rhizogenes*strain which can be used when carrying out the method.

9 Claims, 17 Drawing Sheets

OTHER PUBLICATIONS

Owens et al., 1985, Plant Physiol. 77 (1), pp. 87–94.

Ebbe Truelsen et al., (1979), Nucleic Acids Research, vol. 6, No. 9, "The Primary Structures of Two Leghemoglobin Genes From Soybean".

Jens Jorgen Hyldig-Nielsen et al., (1982), Nucleic Acids Research, vol. 10, No. 2, "Cloning of Soybean Leghemoglobin Structural Gene . . . ".

Ove Wiborg et al., (1982), Nucleic Acids Research, vol. 10, No. 11, "The Nucleotide Sequences of Two Leghemoglobin Genes from Soybean".

Erik Ostergaard Jensen et al., (1981), Nature, vol. 291, No. 5817, pp. 677–679, "The Structure of a Chromosomal Leghemoglobin Gene From Soybean".

Ove Wiborg et al., (1983), The EMBO Journal vol. 2, No. 3, pp. 449–452, "The Structure of an Unusual Leghemoglobin Gene From Soybean".

Kirsten Bojsen et al., (1983), The EMBO Journal vol. 2, No. 7, pp. 1165–1168, "The Chromosomal Arrangement of Six Soybean Leghemoglobin Genes".

Anne Marcker et al., (1984), The EMBO Journal vol. 3, No. 8, pp. 1691–1695, "Transcription of the Soybean Leghemoglobin Genes During . . . ".

Ove Wiborg et al., (1985), The EMBO Journal vol. 4, No. 3, pp. 755–759, "The Human Ubiquitin Multigene Family: Some Genes Contain Multiple . . . ".

Erik Ostergaard Jensen et al., (1986), The EMBO Journal vol. 5, No. 5, pp. 843–847, "Heme Regulates the Expression in *Saccharomyces cervisiae* . . . ".

Erik Ostergaard Jensen et al., (1983), Plant Molecular Biology, pp. 367–379, "The Soybean Leghemoglobin Gene Family".

Jens Stougaard Jensen et al., (1986), Nature, vol. 321, No. 6071, pp. 669–674, "Nodule-Specific Expression of a Chimaeric Soybean Leghemoglobin . . . ".

Annik Petit et al., "Transformation and Regeneration of *Lotus corniculatus*, A System for Molecular Studies of Symbiotic Nitrogen Fixation".

Jens Stougaard Jensen et al., "The Agrobacterium Rhizogenes pRi TL-DNA Segment as a Gene Vector System for Transformation of Plants".

Jorgensen et al., Root Nodule Specific Gene Regulation, 1987, vol. 16, No. 1 1988, Nucleic Acids Research, pp. 39–50.

Sandal et al., A Small Family of Nodule Specific Genes From Soybean, 1987, vol. 15, No. 4, 1987, Nucleic Acids Research, pp. 1507–1519.

Stougaard et al., 5′ Analysis of the Soybean Leghaemoglobin $lbc_3$ Gene: Regulatory Elements Required for Promoter Activity and Organ Specificity, The EMBO Journal, vol. 6, No. 12, pp. 3565–3569, 1987.

```
                                                                                    A   605
------ ------ ---------- -GAGATACA T-TATAATAA TCTCCCTAGT GTCTATTTAT TATTTTATCT GGTGATATAT  C1  664
TTCTCTTAAT ACAATGGAGT TTTTGTTGAA CATACATACA TTTAAAA..AA AATCTTCTAGT GTCTATTTAC CC-------- GGTGAG--AA  C2  639
------ ---TCGAGT TTTTACTGAA CATACATTTA T-TAAAAAAA ACTCTCTAGT GTCCATTTAT TC-------- GGCGAG--AA  C3  751
------ ------ ---------- ---------- --TATGAAGA T-TAAAAAAT ACACTC---- ---------- ---------- ----------

A   568
ACCTTCTCGT ------ ---------- ---------- ---------- ---------- ATACTGTTAT TT--TTT-CA ATCTTGTAGA  C1  578
GCCTTCTCGT GTTTTACACA CTTTAATATT ATTATATCCT CAACCCCAC- --AAAAAAGA ATACTGTTAT ATC-TTTCCA AACCTGTAGA  C2  546
GCCTTCTCGT GCTTTACACA CTTTAATATT ATTATATCCC CACCCCCACC AAAAAAAAAA AAACTGTTAT ATC-TTTCCA -----GTACA  C3  669
------AT ATATATGCCA TAAGAACCAA CAAAAGTACT ATTTAAGAAA AGAAAAAAAA AACCTGTTAT ATAATTTCCA ATCTTGTAGA

A   511
TTTACTTCTT TT------A TTTTTATAAA AAAGACTTTA ---TTTTTT TAAAAA---A ATAAAGTGAA ---------- ---TTATTTA  C1  497
TTTATTTATT TATTTATTTA TTTTTACAAA GGAGACTTCA GAAAAGTAAT TACATAA--- ---------- AGATAGTGAA CATCATT--- ---TTTTTA  C2  473
TTTATTTCTT TT------A TTTTTACAAA GGAAACTTCA CGAAAGTAAT TACAAAA--A ---------- AGATAGTGAA CATCATT--- ---TTTTTAG  C3  590
TTTATTTCTT TT------A TTTTTATAAA GGAGAGTTAA ---AAA--AAT TACAAAATAA ---------- AAATAGTGAA CATCGTCTAA GCATTTTTAT

A   482
---------- TTTTGAAAAC ATGCTCTTTG ACAATTTTC- ---------- ---------- ---------- ---------- ----------  C1  459
TTATAATAAA CTTTAAAATC AAACTTTTTT ATATTTT--- ---------- ---------- ---------- ---------- ----------  C2  434
TTAAGATGAA TTTTAAAATC ACACTTTTTT ATATTTTT-- ---------- ---------- ---------- ---------- ----------  C3  510
ATAAGATGAA TTTTAAAA-- --------T ATAATTTTTT TGTCTCAAATC GTCTGTATCT TGTCTTAGAG CCATTTTTGT TTAAATTGGA

A   440
---------- ---------- ---------- ---------- ---------- ---------- --TG TTTCCTTTTT CATCATTGGG TTAAATCTCA TAGTGCCTCT  C1  417
---------- ---------- ---------- ---------- ---------- --TG TTACCCTTTT CATTATTGGG TGAAATCTCA TAGTGAAGCC  C2  392
---------- ---------- ---------- ---------- ---------- --TG TTACCCTTTT CATTATTGGG TGAAATCTCA TAGTGAAACT  C3  420
TAAGATCACA CTATATAAGTT CTTCCTCCGA GTTTGATATA AAAAAAATTG TTTCCCTTTT GATTATTGGA TAAAATCTCG TAGTGACATT

A   354
ATT---CAAT AATTTGGGCT CAA-TTTAAT TAGTAGAGTC TACATAAAAT TTACCTTAAT AGTAGAGAAT AGAGAGTCTT GGAAAGTTGG  C1  338
ATT----AAAT AATTTGGGCT CAAGTTTTAT TAGTAAAGTC TGCATGAAAT TTAACTTAAC AATAGAGAG- -----AGTTTT CGAAAGG---  C2  313
ATT---AAAT AGTTTGGGCT CAAGTTTTAT TAGTAAAGTC TGCATGAAAT TTAACTTAAT AATAGAGAG- -----AGTTTT GGAAAGG---  C3  338
ATATTAAAAGA AATTAGGGCT CAATTTTTAT TAGTATAGTT TGCATAAATT TTAACTTAAA AATAGAGAA- -----AATCTG GAAAAGG---
```

*FIG. 1A*

| | | | | | | | | | | |
|---|---|---|---|---|---|---|---|---|---|---|
| TTTTTCTCGA | GGAAGAAAGG | AAATGTTAAA | AACTGTGATA | TT------T | TTTTTTTTGA | ----TTAATA | GTTATGTTTA | TATGAAAACT | 275 | A |
| ---------- | ------GAGC | GAATGTTAAA | AAGTGTGATA | TTATA----T | TTTTATTTCGA | ----TTAATA | ATTATGTTTA | CATGAAAACA | 272 | C1 |
| ---------- | ------TAAC | GAATGTTAGA | AAGTGTGATA | TTATTATAGT | TTTATTTAGA | ----TTAATA | ATTATGTTTA | CATGAAAATT | 243 | C2 |
| ---------- | ---------- | GACTGTTAAA | AAGTGTGATA | TTAGA----A | ATTTGTCGGA | TATATTAATA | TTTTATTTTA | TATGGAAACT | 272 | C3 |
| GAAATA-AA | TAAACTAACC | ATATTAAATT | TAGAACAACA | CTTCAATTAT | TTTTTTAAT- | --TTGATTAA | TTAAAAAATT | ATTTGATT-A | 190 | A |
| TACAAAAAAA | TAC------- | -TTTTAAATT | CAGAATAATA | CTTAAAATAT | TTATTTGCTT | AATTGATTAA | CTGAA-AATT | ATTTGATT-A | 192 | C1 |
| GACAA----- | TTTATT---- | -TTTAAAATT | CAGAGTAATA | CTTAAATTAC | TTATTTAC-- | ---------- | ---------- | -----TTTA | 191 | C2 |
| AAAAAAA-TA | TATATTAAAA | -TTTTAAATT | CAGAATAATA | CTTAAATTAT | TTATTTAC-- | ---------- | -TGAA-AATG | AGTTGATTTA | 198 | C3 |
| AATTTTTTAA | AAGATCG-TT | GTTTCTTCTT | CATCATGCTG | ATTGA-CACC | CTCCAC---- | AAGCCAAGAG | AAACACATAA | GCTTTGG--- | 109 | A |
| GGATTTTGAA | AAGATCA-TT | G--GC-TCTT | CGTCATGCCG | ATTGA-CACC | CTCCAC---- | AAGCCAAGAG | AAAC--TTAA | G-TT--GT-A | 117 | C1 |
| AGATTTTGAA | AAGATCATTT | G--GC-TCTT | CATCATGCCG | ATTGA-CACC | CTCCAC---- | AAGCCAAGAG | AAAC--TTAA | G-TT--GT-A | 115 | C2 |
| AGTTTTTGAA | AAGATGA-TT | G--TC-TCTT | CACCATACCA | ATTGATCACC | CTCCTCCAAC | AAGCCAAGAG | AGAC--ATAA | G-TTTATTA | 115 | C3 |
| --TTTTC--- | TCACTCTCCA | AGCCCTCTAT | ATAAACAAAT | ATTGGA-GTG | AAGTTGTTGC | ATAACTTGCA | TCGAACAATT | AATAG-AAAT | 26 | A |
| AACTTTC--- | TCAC--TCCA | AGCCTTCTAT | ATAAACATGT | ATTGGATGTG | AAGTTATTGC | ATAACTTGCA | TTGAACAAT- | ----AGAAAAT | 36 | C1 |
| ATTTTTC--- | TAAC--TCCA | AGCCTTCTAT | ATAAACACGT | ATTGGATGTG | AAGTTGTTGC | ATAACTTGCA | TTGAACAAT- | ---AG-AAAT | 35 | C2 |
| GTTATTCTGA | TCACTCTTCA | AGCCTTCTAT | ATAAATAAGT | ATTGGATGTG | AAGTTGTTGC | ATAACTTGCA | TTGAACAATT | AATAG-AAAT | 26 | C3 |
| AACA--GAAA | ATT------- | --AAAAAAGA | AATATG | 1 | A |
| AACAAAAAAA | AGTAAAAAAG | T-AGAAAAGA | AATATG | 1 | C1 |
| AACA--ACAA | AGAAAATAAG | TGAAAAAAGA | AATATG | 1 | C2 |
| AACA--GAAA | AGT------- | --AGAAAAGA | AATATG | 1 | C3 |

FIG. 1B

SUBCLONES OF THE LBc_3 GENE

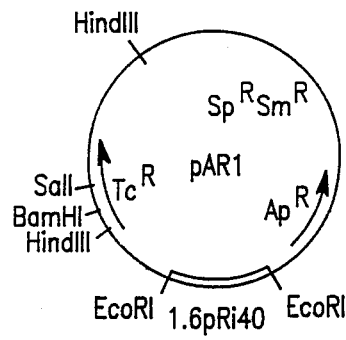
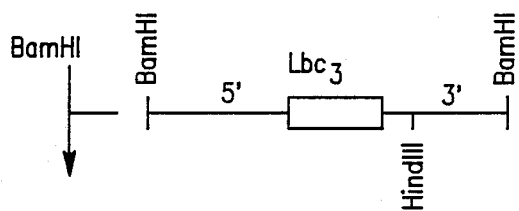
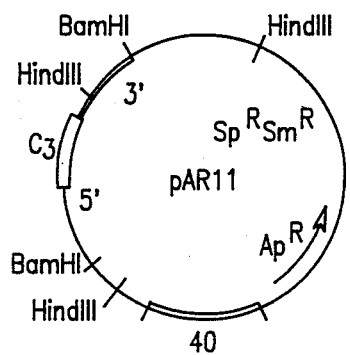
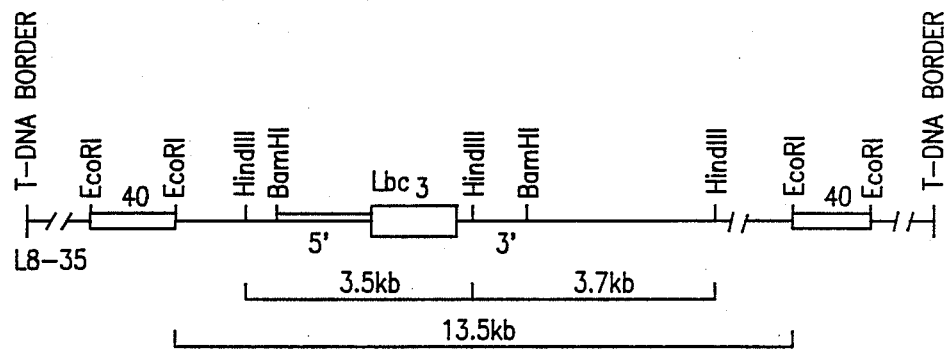
FIG. 7

| | | | | | | | | | | | | |
|---|---|---|---|---|---|---|---|---|---|---|---|---|
| T-AACTTTTT | GAAAACGTCG | -TTG--TG-T | C-TTCATAAT | GCCGATTGA- | TACGCTCGAC | ATTCAATAAG | CCAAGAGAGA | CATATTCAAT | | | | 127 PS1 |
| A-AACTTTTT | GAAAAGATAA | -TTG--TC-T | C-TTCATCAT | TCCGATTGG- | CACCCTGTAC | -------- | CCACAAGAGA | GAC----AT | | | | 131 PS2 |
| T-AAATTTTT | TAAAAGATCG | -TTGTTTCTT | C-TTCATCAT | GCTGATTGA- | CACCCTCCAC | -------- | CCAAGAGAAA | CAC----AT | | | | 118 A |
| T-AGGATTTT | GAAAAGATCA | -TTG--GC-T | C-TTCGTCAT | GCCGATTGA- | CACCCTCCAC | -------- | CCAAGAGAAA | C------TT | | | | 125 C1 |
| TTAAGATTTT | GAAAAGATCA | TTTG--GC-T | C-TTCATCAT | GCCGATTGA- | CACCCTCCAC | -------- | CCAAGAGAAA | C------TT | | | | 123 C2 |
| TTAAGTTTTT | GAAAAGATGA | -TTG--TC-T | C-TTCACCAT | ACCAATTGAT | CACCCTCCTC | ---CAACAAG | CCAAGAGAGA | C------AT | | | | 126 C3 |
| AACAATCCCA | ACAAATTTTT | TTTTTCAGTC | TCCAAACCAT | CTATAT--AA | ACAAGTATTG | GATGTGAACT | T-----ATAA | CT-GGATTGA | | | | 45 PS1 |
| AACCTTTCC- | -----TTTTC | -----TCACTC | TCCAAGACCT | CTATATACAA | ACAAATATTG | GATGTGAAGT | TGTTGCATAA | CTTGCATTGA | | | | 51 PS2 |
| AAGCTTTCG- | -----TTTTC | -----TCACTC | TCCAAGCCCT | CTATAT--AA | ACAAATATTG | GA-GTGAAGT | TGTTGCATAA | CTTGCATCGA | | | | 41 A |
| AAG-TT--GT | --AAACTTTC | -----TCAC-- | TCCAAGCCTT | CTATAT--AA | ACATGTATTG | GATGTGAAGT | TGTTGCATAA | CTTGCATTGA | | | | 48 C1 |
| AAG-TT--GT | --AATTTTTC | -----TAAC-- | TCCAAGCCTT | CTATAT--AA | ACACGTATTG | GATGTGAAGT | TGTTGCATAA | CTTGCATTGA | | | | 46 C2 |
| AAG-TTTAT | T-AGTTATTC | TGA-TCACTC | TTCAAGCCTT | CTATAT--AA | ATAAGTATTG | GATGTGAAGT | TGTTGCATAA | CTTGCATTGA | | | | 41 C3 |
| A-----AATA | GAAATTAAAT | AACA--GAAA | ATTACAA--- | ---AAGATCG | AAATATG | | | | | | | 1 PS1 |
| ACAATTAATA | C-----AAAT | AACA--AGAAA | AGTAAAAAAA | GA-AAAAAAG | AAATATG | | | | | | | 1 PS2 |
| ACAATTAATA | C-----AAAT | AACA--GAAA | ATT------ | ---AAAAAAAG | AAATATG | | | | | | | 1 A |
| ACAAT----A | CA-----AAAT | AACAAAAAAA | AGTAAAAAA- | GT-AGAAAAG | AAATATG | | | | | | | 1 C1 |
| ACAAT----A | C-----AAAT | AACA--ACAA | AGAAAATAA- | GTGAAAAAAG | AAATATG | | | | | | | 1 C2 |
| ACAATTAATA | C-----AAAT | AACA--GAAA | AGT------ | ---AGAAAAG | AAATATG | | | | | | | 1 C3 |

FIG. 8C

METHOD FOR THE EXPRESSION OF GENES IN PLANTS, PARTS OF PLANTS, AND PLANT CELL CULTURES, AND DNA FRAGMENTS, PLASMIDS, AND TRANSFORMED MICROORGANISMS TO BE USED WHEN CARRYING OUT THE METHOD, AS WELL AS THE USE THEREOF FOR THE EXPRESSION OF GENES IN PLANTS

FIELD OF THE INVENTION

The invention relates to a novel method for the expression of genes in plants, parts of plants, and plant cell cultures, as well as DNA fragments and plasmids comprising said DNA fragments to be used when carrying out the method.

The invention relates to this method for the expression of genes of any origin under control of an inducible, rootnodule specific promoter.

The invention relates especially to this method for the expression of root nodule-specific genes in transformed plants including both leguminous plants and other plants.

The invention relates furthermore to DNA fragments comprising an inducible plant promoter to be used when carrying out the method, as well as plasmids comprising said DNA fragments.

In the specification i.a. the following terms are used:

Root nodule-specific genes: Plant genes active only in the root nodules of leguminous plants, or genes with an increased expression in root nodules. Root nodule-specific plant genes are expressed at predetermined stages of development and are activated in a coordinated manner during the symbiosis whereby a nitrogen fixation takes place and the fixed nitrogen is utilized in the metabolism of the plant.

Inducible plant promoter: Generally is meant a promoter-active 5' flanking region from plant genes inducible from a low activity to a high activity. In relation to the present invention "inducible plant promoter" means a promoter derived from, contained in or being identical with a 5' flanking region including a leader sequence of root nodule-specific genes and being capable of promoting and regulating the expression of a gene as characterised in relation to the present invention.

Leader sequence: Generally is meant a DNA sequence being transcribed into a mRNA, but not further translated into protein. The leader sequence comprises thus the DNA fragment from the start of the transcription to the ATG codon constituting the start of the translation. In relation to the present invention "leader sequence" means a short DNA fragment contained in the above inducible plant promoter and typically comprising 40-70 bp and which may comprise sequences being targets for a posttranscriptional regulation.

Promoter region: A DNA fragment containing a promoter which comprises target sequences for RNA polymerase as well as possible activation regions comprising target sequences for transcriptional effector substances. In the present invention, target sequences for transcriptional effectors may also be situated 3' to the promoter, i.e. in the coding sequences, the intervening sequences or on the 3' flanking region of a root nodule-specific gene.

Furthermore a number of molecular-biological terms generally known to persons skilled in the art are used, including the terms stated below:

CAP addition site: The nucleotide where 7-methyl-GTP is added.

DNA sequence or DNA segment: A linear array of nucleotides interconnected through phosphodiester bonds between the 3' and 5' carbon atoms of adjacent pentoses.

Expression: The process undergone by a structural gene to produce a polypeptide. It is a combination of transcription and translation as well as possible post-translational modifications.

Flanking regions: DNA sequences surrounding coding regions. 5' flanking regions contain a promoter. 3' flanking regions may contain a transcriptional terminator etc.

Gene: A DNA sequence composed of three or four parts, viz. (1) the coding sequence for the gene product, (2) the sequences in the promoter region which control whether or not the gene will be expressed, (3) those sequences in the 3' end conditioning the transcriptional termination and optionally polyadenylation, as well as (4) intervening sequences, is any.

Intervening sequences: DNA sequences within a gene which are not coding for any peptide fragment. The intervening sequences are transcribed into pre-mRNA and are eliminated by modification of pre-mRNA and mRNA.

Chimeric gene: A gene composed of parts from various genes. E.g. the chimeric $Lbc_3$-5=-3'-CAT is composed of a chloroamphenicolacetyltransferase-coding sequence deriving from $E.\ coli$ and 5' and 3' flanking regulatory regions of the $Lbc_3$ gene of soybean.

Cloning: The process of obtaining a population of organisms or DNA sequences deriving from one such organism or sequence by asexual reproduction, or more particularly a process of isolating a particular organism or part thereof, and the propagation of this subfraction as a hnomogenous population.

Coding sequences: DNA sequences determining the amino acid sequence of a polypeptide.

Cross-inoculation group: A group of leguminous plant species capable of producing efficient root nodules with Rhizobium bacteria isolated from root nodules of other species of the group.

Leghemoglobin (Lb): An oxygen-binding protein exclusively synthesized in root nodules. The Lb proteins regulate the oxygen tension in the root nodule tissue and transport oxygen to the bacteroids. In this manner the oxygen-sensitive nitrogenase enzyme is protected. The Lb genes are root nodule-specific genes.

Messenger-RNA (mRNA): RNA molecule produced by transcription of a gene and possibly modification of mRNA. The mRNA molecule medites the genetic message determining the amino acid sequence of a polypeptide by part of the mRNA molecule being translated into said peptide.

Downstream: A position in a DNA sequence. It is defined relative to the transcriptional direction 5'→3' of the gene relative to which the position is stated. The 3' flanking region is thus positioned downstream of the gene.

Nucleotide: A monomeric unit of DNA or RNA consisting of a sugar moiety (pentose), a phosphate, and a nitrogeneous heterocyclic base. The base is linked to the sugar moiety via a glycosidic bond (1' carbon of the pentose), and this combination of base and sugar is a nucleoside. The base characterizes the nucleotide. The four DNA bases are adenine (A), guanine (G), cytosine (C), and thymine (T). The four RNA bases are A, G, C and uracil (U).

Upstream: A position in a DNA sequence. It is defined relative to the transcriptional direction 5'→3' of the gene relative to which the position is stated. The 5' flanking region is thus positioned upstream of this gene.

Plant transformation: Processess leading to incorporation of genes in the genome of plant cells in such a manner that these genes are reliably inherited through mitosis and meiosis or in such a manner that these genes are only maintained for short periods.

Plasmid: An extra-chromosomal double-stranded DNA sequence comprising an intact replicon such that the plasmid is replicated in a host cell. When the plasmid is placed within a unicellular organism, the charcteristics of that organism are changed or transformed as a result of the DNA of the plasmid. For instance a plasmid carrying the gene for tetracycline resistance ($Tc^R$) transforms a cell previously sensitive to tetracycline into one which is resistant to it. A cell transformed by a plasmid is called a transformant.

Polypeptide: A linear array of amino acids interconnected by means of peptide bonds between the α-amino and carboxy groups of adjacent amino acids.

Recombination: The creation of a new DNA molecule by combining DNA fragments of different origin.

Replication: A process reproducing DNA molecules.

Replicon: A self-replicating genetic element possessing an origin for the initiation of DNA replication and genes specifying the functions necessary for a control and a replication thereof.

Restriction fragment: A DNA fragment resulting from double-stranded cleavage by an enzyme recognizing a specific target DNA sequence.

RNA polymerase: Enzyme effecting the transcription of DNA into RNA.

Root nodule: Specialized tissue resulting from infection of mainly roots of leguminous plants with Rhizobium bacteria. The tissue is produced by the host plant and comprises therefore plant cells whereas the Rhizobium bacteria upon infection are surrounded by a plant cell membrane and differentiate into bacteroids. Root nodules are produced on other species of plants upon infection of nitrogen-fixing bacteria not belonging to the Rhizobium genus. Root nodule-specific plant genes are also expressed in these nodules.

Southern-hybridization: Denatured DNA is transferred upon size separation in agarose gel to a nitrocellulose membrane. Transferred DNA is analysed for a predetermined DNA sequence or a predetermined gene by hybridization. This process allows a binding of single-stranded, radioactively marked DNA sequences (probes) to complementary single-stranded DNA sequences bound on the membrane. The position of DNA fragments on the membrane binding the probe can subsequently be detected on an X-ray film.

Symbiotic nitrogen fixation: The relationship whereby bacteroids of root nodules convert the nitrogen (dinitrogen) of the air into ammonium utilized by the plant while the plant provides the bacteroids with carbon compounds.

Symbiont: One part of a symbiotic relationship, and especially Rhizobium is called the microsymbiont.

Transformation: The process whereby a cell is incorporating a DNA molecule.

Translation: The process of producing a polypeptide from mRNA or: the process whereby the genetic information present in a mRNA molecule directs the order of specific amino acids during the synthesis of a polypeptide.

Transcription: The method of synthesizing a complementary RNA sequence from a DNA sequence.

Vector: A plasmid, phage DNA or other DNA sequences capable of replication in a host cell and having one or a small number of endonuclease recognition sites at which such DNA sequences my be cleaved in a determinable manner without loss of an essential biological function.

BACKGROUND ART

Traditional plant breeding is based on repeated cross-breeding of plant lines individually carrying desired qualities. The identification of progeny lines carrying all the desired qualities is a particularly time-consuming process as the biochemical and genetic basis of the qualities is usually unknown. New lines are therefore chosen according to their phenotype, usually after a screening of many lines in field experiments.

Through the ages a direct connection has existed between the stage of nutrition, i.e. the health, of the population and the agricultural possibility of ensuring a sufficient supply of nitrogen in order to obtain satisfactory yields. Already in the seventeenth century it was discovered that plants of the family leguminosae including beyond peas also beans, lupins, soybean, bird's-foot trefoil, vetches, alfalfa, sainfoin, and trefoil had an ability of improving crops grown on the habitat of these plants. Today it is known that the latter is due to the fact that the members of the plants of the family leguminosae are able to produce nitrogen reserves themselves. On the roots they carry bacteria with which they live in symbiosis.

An infection of the roots of these leguminous plants with Rhizobium bacteria causes a formation of root nodules able to convert atmospheric nitrogen into bound nitrogen, which is a process called nitrogen fixation.

Atmospheric nitrogen is thereby converted into forms which can be utilized by the host plant as well as by the plants later on growing on the same habitat.

In the nineteenth century the above possibility was utilized for the supply of nitrogen in order to achieve a novel increase of the crop yield.

The later further increases in the yield have, however, especially been obtained by means of natural fertilizers and nitrogen-containing synthetic fertilizers. The resulting pollution of the environment makes it desirable to provide alternative possibilities of ensuring the supply of nitrogen necessary for the best possible yields obtainable.

It would thus be valuable to make an improvement possible of the existing nitrogen fixation systems in leguminous plants as well as to allow an incorporation of nitrogen fixation systems in other plants.

The recombinant DNA technique and the plant transformation systems developed render it now possible to provide plants with new qualities in a well-controlled manner. These characteristics can derive from not only the same plant species, but also from all other procaryotic or eucaryotic organisms. The DNA techniques allow further a quick and specific identification of progeny lines carrying the desired qualities. In this manner a specific plant line can be provided with one or more desired qualities in a quick and well-defined manner.

Correspondingly, plant cells can be provided with well-defined qualities and subsequently be maintained as plant cell lines by means of known tissue culture methods. Such plant cells can be utilized for the production of chemical and biological products of particular interest such as dyes, flavours, aroma components, plant hormones, pharmaceutical products, primary and secondary metabolites as well as polypeptides (enzymes).

A range of factors and functions necessary for biological production of a predetermined gene product are known. Both the initiation and regulation of transcription as well as the initiation and regulation of posttranscriptional processes can be characterised.

At the gene level it is known that these functions are mainly carried out by 5' flanking regions. A wide range of 5' flanking regions from procaryotic and eucaryotic genes has been sequenced, and in view inter alia thereof a comprehensive knowledge has been provided of the regulation of gene expression and of the sub-regions and sequences being of importance for the regulation of expression of the gene. Great differences exist in the regulatory mechanism of procaryotic and eucaryotic organisms, but many common features apply to the two groups.

The regulation of the expression of gene may take place on the transcriptional level and is then preferably exerted by regulating the initiation frequency of transcription. The latter is well known and described inter alia by Benjamin Lewin, Gene Expression, John Wiley & Sons, vol. I, 1974, vol. II, Second Edition 1980, vol. III, 1977. As an alternative the regulation may be exerted at the posttranscriptional level, e.g. by the regulation of the frequency of the translation initiation, at the rate of the translation, and of the termination of the translation.

It has been shown in connection with the present invention that 5' flanking regions of root nodule-specific genes, exemplified by the 5' flanking region of the soybean leghemoglobin $Lbc_3$ gene, can be used for inducible expression of a foreign gene in an alien leguminous plant. The induction and regulation of the promoter is preferably carried out in the form of a regulation and induction at the transcriptional level and differs thereby from the inducibility stated in Danish patent application No. 4889/85, the latter inducibility preferably being carried out at the translation level.

The transcription of both the $Lbc_3$ gene of the soybean and of the chimeric $Lbc_3$ gene transferred to bird's-foot trefoil starts at a low level immediately upon the appearance of the root nodules on the plant roots. Subsequently, a high increase of the transcription takes place immediately before the root nodules turn red. The transcription of a range of other root nodule-specific genes is initiated exactly at this time. The simultaneous induction of the transcription of the Lb genes and other root nodule-specific genes means that a common DNA sequence(s) must be present for the various genes controlling this pattern of expression. Thus the leghemoglobin-$c_3$ gene is a representative of one class of genes and the promoter and the leader sequence, target areas for activation as well as the control elements of the tissue specificity of the $Lbc_3$ gene are representatives of the control elements of a complete gene class.

The promoter of the 5' flanking regions of the Lb genes functions in soybeans and is responsible for the transcription of the Lb genes in root nodules. It is furthermore known, that the efficiency of both the transcription initiation and the subsequent translation initation on the leader sequence of the Lb genes is high as the Lb proteins constitute approximately 20% of the total protein content in root nodules.

The sequence of 5' flanking regions of the four soybean leghemoglobin genes Lba, $Lbc_1$, $Lbc_2$, and $Lbc_3$ appears from the enclosed sequence scheme, scheme 1, wherein the sequences are stated in such a manner that the homology between the four 5' flanking regions appears clearly.

In the sequence scheme "-" indicates that no base is present in the position in question. The names of the genes and the base position counted upstream from the ATG start codon are indicated to the right of the sequence scheme. Furthermore the important sequences have been underlined.

As its appears from the sequence scheme a distinct degree of homology exists between the four 5' flanking regions, and in the position 23-24 bp upstream from the CAP addition site they all contain a TATATAAA sequence corresponding to the "TATA" box which in eukaryotic cells usually are located a corresponding number of bp upstream from the CAP addition site. Furthermore a CCAAG sequence is present 64-72 bp upstream from the CAP addition site, said sequence corresponding to the "CCAAT" box usually located 70-90 bp upstream from the CAP addition site. From the CAP addition site to the translation start codon, ATG, leader sequences of 52-69 bp are present and show a distinct degree of homology of approx. 75-80%.

In accordance with the present invention it has furthermore been proved, exemplified by $Lbc_3$, that the 5' flanking regions of the soybean leghemoglobin genes are functionally active in other plant species. The latter has been proved by fusing the E. coli chloroamphenicol acetyl transferase (CAT) gene with the 5' and 3' flanking regions of the soybean $Lbc_3$ gene in such a manner that the expression of the CAT gene is controlled by the Lb promoter. This fusion fragment was cloned into the integration vectors pAR1 and pAR22, whereby the plasmids pAR29 and pAR30 were produced. Through homologous recombination the latter plasmids were integrated into the Agrobacterium rhizogenes T DNA region. The transformation of Lotus corniculatus (bird's-foot trefoil) plants, i.e. transfer of the T DNA region, was obtained by wound infection on the hypocotyl. Roots developed from the transformed plant cells were taken in in vitro culture and freed from A. rhizogenes bacteria by means of antibiotics. Completely regenerated plants were produced by these root cultures through somatic embryogenesis or organogenesis.

Regenerated plants were subsequently inoculated with Rhizobium loti bacteria and root nodules for analysis were harvested. Transcription and translation of the chimeric $Lbc_3$ CAT gene could subsequently be detected in root nodules on transformed plants as the activity of the produced chloroamphenicol acetyl transferase enzyme.

The conclusion can subsequently be made that the promoter-containing 5' flanking regions of root nodule-specific genes exemplified by the soybean $Lbc_3$ promoter are functionally active in foreign plants. The latter is a surprising observation as root nodules are only developed as a consequence of a very specific interaction between the leguminous plant and its corresponding Rhizobium microsymbiont.

Soybeans produce nodules only upon infection by the species Rhizobium japonicum and Lotus corniculatus only upon infection by the species Rhizobium loti. Soybean and *Lotus corniculatus* belong therefore to two different cross-inoculation groups, each group producing root nodules by means of two different Rhizobium species. The expression of a chimeric soybean gene in *Lotus corniculatus* proves therefore an unexpected universal regulatory system applying to the expression of root nodule-specific genes. The regulatory DNA sequences involved can be placed on the 5' and 3' flanking regions of the genes, here exemplified by the 2.0 Kb 5' and 0.9 Kb 3' flanking regions of the Lbc$_3$ gene. This observation allows the use of root nodule-specific promoters and regulatory sequences in any other plant species and any other plant cell line.

OBJECTS OF THE INVENTION

An object of the present invention is to provide a possibility of expressing desired genes in plants, parts of plants, and plant cell cultures.

A further object of the invention is to render it possible to express genes of any origin by the control of an inducible root nodule-specific promoter.

A particular object of the invention is to provide a possibility of expressing desired genes in leguminous plants.

A still further particular object of the invention is to provide a possibility of expressing root nodule-specific genes in non-leguminous plants.

Further objects of the invention are to improve the existing nitrogen-fixing systems in leguminous plants as well as to incorporate nitrogen-fixing systems in other plants.

A further object of the invention is to provide a possibility of in certain cases allowing the use of specific sequences of the 3' flanking region, of the coding sequence, and of intervening sequences to influence the regularity of the root nodule-specific promoter.

Furthermore it is an object of the invention to provide plasmids comprising the above mentioned inducible plant promoter.

Futher objects of the invention appear immediately from the following description.

DESCRIPTION OF THE INVENTION

These objects are obtained by carrying out the method according to the invention for the expression of genes in plants, parts of plants, and plant cell cultures, said method being characterised by using a DNA fragment comprising an inducible plant promoter from root nodule-specific genes.

The method according to the invention allows in a well-defined manner an expression of foreign genes in plants, parts of plants, and plant cell cultures, in this connection especially genes providing the plants with desired properties such as for instance a resistance to plant diseases and increased content of valuable polypeptides.

A further use is the preparation of valuable products such as for instance dyes, flavourings, plant hormones, pharmaceutical products, primary and secondary metabolites, and polypeptides by means of the method according to the invention in plant cell cultures and plants.

By using the method according to the invention for the expression of root nodule-specific genes it is possible to express root-nodule-specific genes necessary for the formation of an active nitrogen-fixing system both in leguminous plants and other plants. The correct developmental control, cf. Example 8, allows the establishment of a symbiotic nitrogen-fixing system in non-leguminous plants. In this manner it is surprisingly possible to improve the existing nitrogen-fixing systems in leguminous plants as well as to incorporate nitrogen-fixing systems in other plants.

The use of the method according to the invention for the expression of foreign genes in root nodules renders it possible to provide leguminuous plants with improved properties such as resistance to herbicides and resistance to diseases and pests.

According to a particular embodiment of the method according to the invention a DNA fragment is used which comprises an inducible plant promoter and which is identical with, derived from, or comprises 5' flanking regions of leghemoglobins. In this manner the expression of any gene is obtained.

Examples of such DNA fragments are DNA fragments of the four 5' flanking regions of the soybean leghemoglobin genes, viz.

Lba with the sequence:

```
GAGATACATT  ATAATAATCT  CTCTAGTGTC  TATTTATTAT  TTTATCTGGT
GATATATACC  TTCTCGTATA  CTGTTATTTT  TTCAATCTTG  TAGATTTACT
TCTTTTATTT  TTATAAAAAA  GACTTTATTT  TTTTAAAAAA  AATAAAGTGA
ATTTTGAAAA  CATGCTCTTT  GACAATTTTC  TGTTTCCTTT  TTCATCATTG
GGTTAAATCT  CATAGTGCCT  CTATTCAATA  ATTTGGGCTC  AATTTAATTA
GTAGAGTCTA  CATAAAATTT  ACCTTAATAG  TAGAGAATAG  AGAGTCTTGG
AAAGTTGGTT  TTTCTCGAGG  AAGAAAGGAA  ATGTTAAAAA  CTGTGATATT
TTTTTTTTGG  ATTAATAGTT  ATGTTTATAT  GAAAACTGAA  AATAAATAAA
CTAACCATAT  TAAATTTAGA  ACAACACTTC  AATTATTTTT  TTAATTTGAT
TAATTAAAAA  ATTATTTGAT  TAAATTTTTT  AAAAGATCGT  TGTTTCTTCT
TCATCATGCT  GATTGACACC  CTCCACAAGC  CAAGAGAAAC  ACATAAGCTT
TGGTTTTCTC  ACTCTCCAAG  CCCTCTATAT  AAACAAATAT  TGGAGTGAAG
TTGTTGCATA  ACTTGCATCG  AACAATTAAT  AGAAATAACA  GAAAATTAAA
AAAGAAATAT  G,
```

Lbc$_1$ with the sequence:

```
TTCTCTTAAT  ACAATGGAGT  TTTTGTTGAA  CATACATACA  TTTAAAAAAA
AATCTCTAGT  GTCTATTTAC  CCGGTGAGAA  GCCTTCTCGT  GTTTTACACA
CTTTAATATT  ATTATATCCT  CAACCCCACA  AAAAAGAATA  CTGTTATATC
TTTCCAAACC  TGTAGATTTA  TTTATTTATT  TATTTATTTT  TACAAAGGAG
ACTTCAGAAA  AGTAATTACA  TAAAGATAGT  GAACATCATT  TTATTTATTA
TAATAAACTT  TAAAATCAAA  CTTTTTTATA  TTTTTTGTTA  CCCTTTTCAT
TATTGGGTGA  AATCTCATAG  TGAAGCCATT  AAATAATTTG  GGCTCAAGTT
TTATTAGTAA  AGTCTGCATG  AAATTTAACT  TAACAATAGA  GAGAGTTTTC
GAAAGGGAGC  GAATGTTAAA  AAGTGTGATA  TTATATTTTA  TTTCGATTAA
```

-continued
```
TAATTATGTT  TACATGAAAA  CATACAAAAA  AATACTTTTA  AATTCAGAAT
AATACTTAAA  ATATTTATTT  GCTTAATTGA  TTAACTGAAA  ATTATTTGAT
TAGGATTTTG  AAAAGATCAT  TGGCTCTTCG  TCATGCCGAT  TGACACCCTC
CACAAGCCAA  GAGAAACTTA  AGTTGTAAAC  TTTCTCACTC  CAAGCCTTCT
ATATAAACAT  GTATTGGATG  TGAAGTTATT  GCATAACTTG  CATTGAACAA
TAGAAAATAA  CAAAAAAAG   TAAAAAAGTA  GAAAGAAAT   ATG,
```

Lbc₂ with the sequence:

```
TCGAGTTTTT  ACTGAACATA  CATTTATTAA  AAAAAACTCT  CTAGTGTCCA
TTTATTCGGC  GAGAAGCCTT  CTCGTGCTTT  ACACACTTTA  ATATTATTAT
ATCCCCACCC  CCACCAAAAA  AAAAAAAACT  GTTATATCTT  TCCAGTACAT
TTATTTCTTA  TTTTTACAAA  GGAAACTTCA  CGAAAGTAAT  TACAAAAAAG
ATAGTGAACA  TCATTTTTTT  AGTTAAGATG  AATTTTAAAA  TCACACTTTT
TTATATTTTT  TTGTTACCCT  TTTCATTATT  GGGTGAAATC  TCATAGTGAA
ACTATTAAAT  AGTTTGGGCT  CAAGTTTTAT  TAGTAAAGTC  TGCATGAAAT
TTAACTTAAT  AATAGAGAGA  GTTTTGGAAA  GGTAACGAAT  GTTAGAAAGT
GTGATATTAT  TATAGTTTTA  TTTAGATTAA  TAATTATGTT  TACATGAAAA
TTGACAATTT  ATTTTTAAAA  TTCAGAGTAA  TACTTAAATT  ACTTATTTAC
TTTAAGATTT  TGAAAAGATC  ATTTGGCTCT  TCATCATGCC  GATTGACACC
CTCCACAAGC  CAAGAGAAAC  TTAAGTTGTA  ATTTTTCTAA  CTCCAAGCCT
TCTATATAAA  CACGTATTGG  ATGTGAAGTT  GTTGCATAAC  TTGCATTGAA
CAATAGAAAT  AACAACAAAG  AAAATAAGTG  AAAAAAGAAA  TATG,
``` and Lbc₃ with the sequence:

```
TATGAAGATT  AAAAAATACA  CTCATATATA  TGCCATAAGA  ACCAACAAAA
GTACTATTTA  AGAAAGAAA   AAAAAAACCT  GCTACATAAT  TTCCAATCTT
GTAGATTTAT  TTCTTTTATT  TTTATAAAGG  AGAGTTAAAA  AAATTACAAA
ATAAAAATAG  TGAACATCGT  CTAAGCATTT  TTATATAAGA  TGAATTTTAA
AAATATAATT  TTTTTGTCTA  AATCGTATGT  ATCTTGTCTT  AGAGCCATTT
TTGTTTAAAT  TGGATAAGAT  CACACTATAA  AGTTCTTCCT  CCGAGTTTGA
TATAAAAAAA  ATTGTTTCCC  TTTTGATTAT  TGGATAAAAT  CTCGTAGTGA
CATTATATTA  AAAAAATTAG  GGCTCAATTT  TTATTAGTAT  AGTTTGCATA
AATTTTAACT  TAAAAATAGA  GAAAATCTGG  AAAAGGGACT  GTTAAAAAGT
GTGATATTAG  AAATTTGTCG  GATATATTAA  TATTTTATTT  TATATGGAAA
CTAAAAAAAT  ATATATTAAA  ATTTTAAATT  CAGAATAATA  CTTAAATTAT
TTATTTACTG  AAAATGAGTT  GATTTAAGTT  TTTGAAAAGA  TGATTGTCTC
TTCACCATAC  CAATTGATCA  CCCTCCTCCA  ACAAGCCAAG  AGAGACATAA
GTTTTATTAG  TTATTCTGAT  CACTCTTCAA  GCCTTCTATA  TAAATAAGTA
TTGGATGTGA  AGTTGTTGCA  TAACTTGCAT  TGAACAATTA  ATAGAAATAA
CAGAAAAGTA  GAAAAGAAAT  ATG.
```

By a particular embodiment of the method according to the invention a 3' flanking region of root nodule-specific genes is furthermore used. In this manner it is possible to utilize when the 3' flanking region comprises sequences capable of influencing the activity or regularity of the root nodule promoter or the transcription termination, or capable of influencing the yield of the desired gene product in another manner.

Examples of such 3' flanking regions are the four 3' flanking regions of the soybean leghemoglobin genes, viz.

Lba with the sequence:

```
                1590
TAA TTA GTA TCT ATT GCA GTA AAG TGT AAT AAA
                1620
TAA ATC TTG TTT CAC TAT AAA ACT TGT TAC TAT
                1650
TAG ACA AGG GCC TGA TAC AAA ATG TTG GTT AAA
1680                                    1710
ATA ATG GAA TTA TAT AGT ATT GGA TAA AAA TCT
                1740
TAA GGT TAA TAT TCT ATA TTT GCG TAG GTT TAT
                1770
GCT TGT GAA TCA TTA TCG GTA TTT TTT TTC CTT
                1800
TCT GAT AAT TAA TCG GTA AAT TA ACA AAT AAG
                1830
TTC AAA ATG ATT TAT ATG TTT CAA AAT TAT TTT
                1860
AAC AGC AGG TAA AAT GTT ATT TGG TAC GAA AGC
            TAA TTC GTC GA
```

Lbc₁ with the sequence:

```
                1320
TAA/TT AGG ATC TAC TGC ATT GCC GTA AAG TGT
                1350
AAT AAA TAA ATC TTG TTT CAA CTA AAA CTT GTT
                1380
ATT AAA CAA GTT CCC TAT ATA AAT GTT GTT TAA
                1410
AAT AAG TAA ATT TCA TTG TAT TGG ATA AAC ACT
                1440
TTT AAG TTA TAT ATT TCC ATA TAT TTA CGT TTG
                1470
TGA ATC ATA ATC GAT ACT TTA TAA AAA TAA ATT
                1500
CCA AAT AAT TTA TAC GTT TTA AAA ATT ATT TT
```

Lbc₂ with the sequence:

```
                                               TAG/GAT CTA CTA TTG CCG TCA AGT
                                                              1140
GTA ATA AAT AAA TTT TGT TTC ACT AAA ACT TGT TAT TAA ACA AGT CCC CGA TAT ATA AAT
                  1170                                                    1200
GTT GGT TAA AAT AAG TAA ATT ATA CGG TAT TGA TAA ACA ATC TTA AGT TTT ATA TAT AGT
                  1230                                                    1260
TCC ATA TAC TAA AGT TTG TGA ATC ATA ATC GA
                  1290
``` and Lbc₃ with the sequence:

```
                   TAG/GAT CTA CAA TTG CCT TAA AGT GTA ATA AAT AAA
                          990                                1020
TAT TAT TTC ACT AAA ACT TGT TAT TAA ACC AAG TTC TCG ATA TAA ATG TTG GTT AAA CTA
              1050                                                    1080
AGT AAA TTA TAT GGT ATT GGA TAA ACA ATC TTA AGC TT
                  1110
```

This sequence is positioned on the 0.9 Kb 3' flanking region used according to the invention. A particular embodiment of the invention is therefore the use of sequences of this region exerting or mediating the regulation characterized by the invention of root nodule-specific promoter regions.

In a preferred embodiment of the method according to the invention a region is used of the coding sequence or intervening sequence of root nodulespecific genes, in particular sequences of the coding sequence or the intervening sequence capable of influencing the regulation of a promotor of the root nodule-specific genes or capable of influencing the yield of the desired gene product in another manner.

Examples of such coding sequences and intervening sequences are the four leghemoglobin genes of soybean, viz.

Lba with the sequence:

```
                                                                               120
                                                                               VAL
                                                                               ATG/GTT
                                    150                                        180
        ALA PHE THR GLU LYS  GLN ASP ALA LEU VAL SER SER  SER PHE GLU ALA PHE LYS ALA ASN
        GCT TTC ACT GAG AAG CAA GAT GCT TTG GTG AGT AGC TCA TTC GAA GCA TTC AAG GCA AAC 210                                        240
        ILE PRO GLN TYR SER  VAL VAL PHE TYR THR SER
        ATT CCT CAA TAC AGC GTT GTG TTC TAC ACT TC/G TAA GTT TTC TCT CTA AGC ATG TGT CTT 270                                        300
        CCA TTC TAT GTT TTT CTT TTG GAA ATT TGT TGT GTT TGA AAA AAG ATA TAT TGT TAA TGT 330                                        360
                                                ILE LEU GLU LYS ALA PRO ALA ALA LYS ASP
        GAG TGG TTT TGG TTT GAT TAA AAA TGA ATAG/G ATA CTG GAG AAA GCA CCT GCA GCA AAG GAC 390                                        420
        LEU PHE SER PHE LEU ALA ASN GLY VAL ASP PRO THR ASN PRO LYS LEU THR GLY HIS ALA
        TTG TTC TCA TTT CTA GCA AAT GGA GTA GAC CCC ACT AAT CCT AAC CTC ACG GGC CAT GCT 450                                        480
        GLU LYS LEU PHE ALA LEU
        GAA AAG CTT TTT GCA TTG/GTAA GTA TCA CCC AAC TAA AAT TAT AAC TAT TTT ATG TGA 510                                        540
        TTA ATT TTA AGA TTA AGC ATC ATG TAT TTT AAC ACT CTT AAA ACA TCA ATG AAC ATT AAT 570                                        600
        TGT TTG AAT TGT ATT TTA TAT TTT TGC CAT ATC TTG AAC TAG GAA TAG TAT ATA AAT TTC 630                                        660
        TAT TAG TAT TTG TTG ATA ATT ATT TTT CTT TCA TAA CTA TCT TGT CAC ATA TTA TAT ATT 690                                        720
                VAL ARG ASP SER ALA GLY GLN LEU LYS ALA SER  GLY THR VAL VAL ALA
        TTT TGA ATT GTAG/GTG CGT GAC TCA GCT GGT CAA CTT AAA GCA AGT GGA ACA GTG GTG GCT 750                                        780
        ASP ALA ALA LEU GLY SER VAL HIS  ALA GLN LYS ALA VAL THR ASP PRO GLN PHE VAL
        GAT GCC GCA CTT GGT TCT GTT CAT GCC CAA AAA GCA GTC ACT GAT CCT CAG TTC GTG/GT 810                                        840
        ATG ATA AAT AAT GAA ATG TTA TAA TAA ATT ATG CAT ACT TCA ATT TTT CAT GGA GCA GTA
```

-continued

```
                        870                                              900
TAA TGA TCA ACA CAC ACT TCT TTT GTT TCA TGC ATT TGA TAA CTA CAA TCT TAA AAT GTT 930                                              960
GCA ATC TTA AAA ATA GTA TTA AAA ATA TAA CAT TTA ATT AGC TCA TCA ATA TTT TTC TGT 990                                             1020
TGC AAT TTT TTA TGA AAA AAT TAT AAT TAT GAA TTC TTT GAG CAA TGT TTA ATT AAA AAA 1050                                             1080
TTG ATT TAA TAA TGA AAT AAC TAA GCT ACC TCT GTC TCG TTT TTC ATT TAA ACT ATG ACA 1110                                             1140
TAA ACA ATG AAT AAA GTA AAC TAA ACC ATG ACA TGT TTA TTT TTG AAT GAG GTT ATT AAT 1170                                             1200
AAT TTT TTT TCA CTA TCT ATT GCA ATG TTC ATT GAT TAT CAA TTA TCT TGG TTG CAT TGA 1230                                             1260
TTC TCT CGA TTT TTT TCT TGA GGT TAA GCT TCA GTT CAA TAT ATA TTC ATT TTT TGA TAA 1290                                             1320
AAA AAA ATA GTA CAA TAT ATT TTC ATT TAG CTG ATC ATA TTT ATT TAA GTT CAA CTT AAA 1350                                             1380
ATT TTA TAG ATG TTA ATT GAT ATA ATT TGT TGA GAT GAT GAG AAG ACC AAT ACC ATT ACG 1410                                             1440
TAC TCT TTT GAA AGT GTT ATA TGG ATT TTA ATT ATA AGG AAA AAT GTA AGA GCT AAA CCA 1470                                             1500
                    VAL VAL LYS GLU ALA LEU LEU LYS THR ILE LYS ALA ALA VAL
TTG CTG ATG ATT TTG AAG/GTG GTT AAA GAA GCA CTG CTG AAA ACA ATA AAG GCA GCA GTT 1530                                             1560
GLY ASP LYS TRP SER ASP GLU LEU SER ARG ALA TRP GLU VAL ALA TYR ASP GLU LEU ALA
GGG GAC AAA TGG AGT GAC GAG TTG AGC CGT GCT TGG GAA GTA GCC TAC GAT GAA TTG GCA

ALA ALA ILE LYS LYS ALA
GCA GCT ATT AAG AAG GCA TAA
```

The amino acid sequence of the Lba protein is indicated above the coding sequence, Lbc₁ with the sequence:

```
                                                                         180
                                                                         GLY
                                                                         ATG/GCT
                                  210                                    240
ALA PHE THR GLU LYS GLN GLU ALA LEU VAL SER SER SER PHE GLU ALA PHE LYS ALA ASN
GCT TTC ACT GAG AAG CAA GAG GCT TTG GTG AGT AGC TCA TTC GAA GCA TTC AAG GCA AAC 270                                    300
ILE PRO GLN TYR SER VAL VAL PHE TYR ASN SER
ATT CCT CAA TAC AGC GTT GTG TTC TAC AAT TC/GTAA GTT TTC TCT ATA AGC ATG TGT CTT 330                                    360
TCA TTC TAT GTT TTT CTT CTG GAA ATT TTT TGT GTT TGA AAA AAG ATA TAT ATA TAT ATA 390                                    420
TAT ATA TAT ATA TAT ATA TAT ATA TAT ATA TAT ATA TAT TTT GTT AAT GTG AGT GGT TTT 450                                    480
                           ILE LEU GLU LYS ALA PRO ALA ALA LYS ASP LEU PHE SER
GGT TTG ATT AAA AAT AAA TAG/GATT CTG GAG AAA GCA CCT GCA GCA AAG GAC TTG TTC TCA 510                                    540
PHE LEU ALA ASN GLY VAL ASP PRO THR ASN PRO LYS LEU THR GLY HIS ALA GLU LYS LEU
TTT CTA GCA AAT GGA GTA GAC CCC ACT AAT CCT AAG CTC ACG GGC CAT GCT GAA AAG CTT 570                                    600
PHE ALA LEU
TTT GCA TTG/GT AAG TAT CAG CCA ACT AAA ATT ATA ACT ATT TTA TGT GAT TAA TTT TAA 630                                    660
GAT TAA ACA TCA TGT ATT TTA ACA CTC TTA AAA TAT CAA TGA ACA TTA ATT TTT TGA ATT 690                                    720
GTA TTT TAT ATT TTT ACC ATA TCT TGA ACT AGG AAT AAT ATA TAA ATT TCT ATT AGT ATT
```

```
                                          750                                                    780
TGT TGG TAA TTA CAT ATA TAT ATA TAT ATA TAA TCC TTG TGA TAA TTA TTT TTC GAA TTT

VAL ARG ASP SER ALA GLY GLN LEU LYS THR ASN GLY THR VAL VAL ALA ASP ALA ALA
            GTAG/GTG CGT GAC TCA GCT GGT CAA CTT AAA ACA AAT GGA ACA GTG GTG GCT GAT GCT GCA 870                                                    900
LEU VAL SER ILE HIS ALA GLN LYS ALA VAL THR ASP PRO GLN PHE VAL
CTT GTT TCT ATC CAT GCC CAA AAA GCA GTC ACT GAT CCT CAG TTC GTG/GT ATG ATA AAT 930                                                    960
AAT ACT AGT AAA ATG TTA CAA TAA ATG CAA ACT TAA GTT TTA CGT ACA TAG TGA TCA TGA 990                                                    1020
CTT CAT GCA TGG CTA TTA TTT TTT CAT ATT TAT TGA AGT CAA CTT AAA ATT TTG TAA ATA 1050                                                   1080
CAG ATC GAT GCT AGT AAT TTG TTG AGA TCA TGA GAA AAC GTA CCA CTA CTC CAA TAG CAT 1110                                                   1140
TAC TCA TTT TGA AAA TTG TAT AAC TGT GAT CTA ATT ATA AGG AAA AAG TGT ATA TAA GAG 1170                                                   1200
                                                    VAL VAL LYS GLU ALA LEU LEU LYS THR
CTA ATC CAT TAT TAA TGT TTT TTA TAT TTT GTAG/GTG GTT AAA GAA GCA CTG CTG AAA ACA 1230                                                   1260
ILE LYS GLU ALA VAL GLY GLY ASN TRP SER ASP GLU LEU SER SER ALA TRP GLU VAL ALA
ATA AAG GAA GCT GTT GGC GGC AAT TGG AGT GAC GAA TTG AGC AGT GCT TGG GAA GTA GCC

1290
TYR ASP GLU LEU ALA ALA ALA ILE LYS LYS ALA
TAT GAT GAA TTG GCA GCA GCA ATT AAA AAG GCA TAA
```

The amino acid sequence of the Lbc$_1$ protein is indicated above the coding sequence.

Lbc$_2$ with the sequence:

```
                                                                                GLY
                                                                                G/GGT
                                                                                180

ALA PHE THR GLU LYS GLN GLU ALA LEU VAL SER SER SER PHE GLU ALA PHE LYS ALA ASN
GCT TTC ACT GAG AAG CAA GAG GCT TTG GTG AGT AGC TCA TTC GAA GCA TTC AAG GCA AAC
                                          210                                                    240

ILE PRO GLN TYR SER VAL VAL PHE TYR THR SER
ATT CCT CAA TAC AGC GTT GTG TTC TAC ACT TC/GTA AGT TTT CTC TTA AAG CAT GTA TCT
                                          270                                                    300

TTC ATT CTC TGT TTT TCC TTT CGA CAT TTT TTG TGT TTG AAA AGA GAT AGT GTC AAT GTG
                                          330                                                    360

ILE LEU GLU LYS ALA PRO ALA ALA LYS
AGT GGG TAT TTT TTT TTA TTA AAA ATT AAC AG/G ATA CTG GAG AAA GCA CCC GCA GCA AAG
                                          390                                                    420

ASP LEU PHE SER PHE LEU SER ASN GLY VAL ASP PRO SER ASN PRO LYS LEU THR GLY HIS
GAC TTG TTC TCG TTT CTA TCT AAT GGA GTA GAT CCT AGT AAT CCT AAG CTC ACG GGC CAT
                                          450                                                    480

ALA GLU LYS LEU PHE GLY LEU
GCT GAA AAG CTT TTT GGA TTG/GTA AGT ATC ATC CAA CTA AAA TTA TAG CTA TTT TAT GTG
                                          510                                                    540

ATT AAT TTT AAG ATT AAA CAT GTA TTT AAC ACT CTT AAA CAT GTA TTT AAC ACT CTT AAG
                                          570                                                    600

ATT AAA CAT GTA TTT AAC TAA AAC ATG TAT TTG CTG ATT ATT TTT TTT TTA TAA TTA TCT
                                          630                                                    660

VAL ARG ASP SER ALA GLY GLN LEU LYS ALA
TGT CAC ATA TTA TAT ATT TTT TGA ATT GTA G/GTG CGT GAC TCA GCT GGT CAA CTT AAA GCA
                                          690                                                    720

ASN GLY THR VAL VAL ALA ASP ALA ALA LEU GLY SER ILE HIS ALA GLN LYS ALA ILE THR
AAT GGA ACA GTA GTG GCT GAT GCC GCA CTT GGT TCT ATC CAT GCC CAA AAA GCA ATC ACT
                                          750                                                    780
```

```
                                        ASP PRO GLN PHE VAL
GAT CCT CAG TTC GTG/GT ATG ATA AAT AAT AAA ATG TTA CAA TAA ATG CAC ATA TAC TTA
                810                                                     840

AAT TTT ACA TGG TGC AGT GTT ATG ATC ATC ATT TTT GTT TAG TAA TGA ATT TAC TTA AAA
                870                                                     900

TCT TAA ATT ATG TAC TTT TTG AAA GTT TTA TAT GGA ATT TTA ATT ATA GGG AAA AAT GTA
                930                                                     960

VAL VAL LYS GLU ALA LEU LEU LYS THR
AGA GCT AAT CCA TTA GTG ATG TTT TGT CTG TAG/GTG GTT AAA GAA GCA CTG CTG AAA ACA
                990                                                    1020

LE LYS GLU ALA VAL GLY ASP LYS TRP SER ASP GLU LEU SER SER ALA TRP GLU VAL ALA
ATA AAG GAG GCA GTT GGG GAC AAA TGG AGT GAT GAA TTG AGC AGT GCT TGG GAA GTA GCC
               1050                                                    1080

TYR ASP GLU LEU ALA ALA ALA ILE LYS LYS ALA PHE
TAT GAT GAA TTG GCA GCA GCT ATT AAG AAG GCA TTT TAC
                                                1110
```

The amino acid sequence of the Lbc$_2$ protein is indicated above the coding sequence.

Lbc$_3$ with the sequence:

```
                                                        GLY ALA PHE THR ASP
                                                      G/GGT GCT TTC ACT GAT
                                                                        120

LYS GLN GLU ALA LEU VAL SER SER SER PHE GLU ALA PHE LYS THR ASN ILE PRO GLN TYR
AAG CAA GAG GCT TTG GTG AGT AGC TCA TTT GAA GCA TTC AAG ACA AAC ATT CCT CAA TAC
                150                                                     180

SER VAL VAL PHE TYR THR SER
AGT GTT GTG TTC TAC ACC TC/GTA AGT ATT CTA TCT AAA TTA TGT GTC TTA TTG TAT GTT
                210                                                     240

TAA CTT TCG TGG TTT GTT GTG TTT GAA AAA AAG ATA TAT ATT GTT AAT GTG AGT GGT TTT
                270                                                     300

ILE LEU GLU LYS ALA PRO VAL ALA LYS ASP LEU PHE SER
GGT TTG ACT AAA AAT GAA TAG/G ATA CTG GAG AAA GCA CCT GTA GCA AAG GAC TTG TTC TCA
                330                                                     360

PHE LEU ALA ASN GLY VAL ASP PRO THR ASN PRO LYS LEU THR GLY HIS ALA GLU LYS LEU
TTT CTA GCT AAT GGA GTA GAC CCC ACT AAT CCT AAG CTC ACG GGC CAT GCT GAA AAA CTT
                390                                                     420

PHE GLY LEU
TTT GGA TTG/GT AAG TAT CCA GCC TAC TAA AAT TAA AAT CCT ATT AGT ATT TTT TAT TAT
                450                                                     480

VAL ARG ASP SER
TTT TCT TCC ATG ATT GTC TTG TCA CAT ATT ATA TAT TTT TTG AAT TAT AG/GTA CGT GAT TCA
                510                                                     540

ALA GLY GLN LEU LYS ALA SER GLY THR VAL VAL ILE ASP ALA ALA LEU GLY SER ILE HIS
GCT GGT CAA CTT AAA GCA AGT GGA ACA GTG GTG ATT GAT GCC GCA CTT GGT TCT ATC CAT
                570                                                     600

ALA GLN LYS ALA ILE THR ASP PRO GLN PHE VAL
GCC CAA AAA GCA ATC ACT GAT CCT CAA TTT GTG/G TAT GAT AAA TAA TGA AAA GCT ACA
                630                                                     660

ATA AAT GCA CAA ATA CTT AAT TTT ACA TAG TGC AGT GCT ATA TGA TCA TCA CTT TTG CTT
                690                                                     720

AGT AAT GAA TTT ACT TTT TTT TTT TAC AGA AGT AAT GGA TTT ACT TAA AAT CTT AAA TTA
                750                                                     780

TGT ACT TCT TTA AAG AGT TTT GTA TGG AAT TTT AAT TAT AGG AAA AAT GTA AGA GCT AAA
                810                                                     840

VAL VAL LYS GLU ALA LEU LEU LYS THR ILE LYS GLU ALA
CCA TTG CTG ATG ATT TCG AAG/GTG GTT AAA GAA GCA CTG CTG AAA ACA ATA AAG GAG GCA
                870                                                     900
```

-continued

```
VAL GLY ASP LYS TRP SER ASP GLU LEU SER SER ALA TRP GLU VAL ALA TYR ASP GLU LEU
GTT GGG GAC AAA TGG AGT GAC GAG TTG AGC AGT GCT TGG GAA GTA GCC TAT GAT GAA TTG
                              930                                              960

ALA ALA ALA ILE LYS LYS ALA PHE
GCA GCA GCT ATT AAG AAG GCA TTT TAG
```

The amino acid sequence of the Lbc₃ protein is indicated above the coding sequence.

The present invention furthermore deals with a novel DNA fragment comprising an inducible plant promoter to be used when carrying out the method according to the invention, said DNA fragment being characterised by being identical with, derived from or comprising a 5' flanking region of root nodule-specific genes. Examples of such DNA fragments are DNA fragments being identical with, derived from or comprising a 5' flanking region of plant leghemoglobin genes. Examples thereof are according to the invention DNA fragments being identical with, derived from or comprising a 5' flanking region of the four soybean leghemoglobin genes, viz.:

Lba with the sequence:

```
GAGATACATT  ATAATAATCT  CTCTAGTGTC  TATTTATTAT  TTTATCTGGT
GATATATACC  TTCTCGTATA  CTGTTATTTT  TTCAATCTTG  TAGATTTACT
TCTTTTATTT  TTATAAAAAA  GACTTTATTT  TTTTAAAAAA  AATAAAGTGA
ATTTTGAAAA  CATGCTCTTT  GACAATTTTC  TGTTTCCTTT  TTCATCATTG
GGTTAAATCT  CATAGTGCCT  CTATTCAATA  ATTTGGGCTC  AATTTAATTA
GTAGAGTCTA  CATAAAATTT  ACCTTAATAG  TAGAGAATAG  AGAGTCTTGG
AAAGTTGGTT  TTTCTCGAGG  AAGAAAGGAA  ATGTTAAAAA  CTGTGATATT
TTTTTTTTGG  ATTAATAGTT  ATGTTTATAT  GAAAACTGAA  AATAAATAAA
CTAACCATAT  TAAATTTAGA  ACAACACTTC  AATTATTTTT  TTAATTTGAT
TAATTAAAAA  ATTATTTGAT  TAAATTTTTT  AAAAGATCGT  TGTTTCTTCT
TCATCATGCT  GATTGACACC  CTCCACAAGC  CAAGAGAAAC  ACATAAGCTT
TGGTTTTCTC  ACTCTCCAAG  CCCTCTATAT  AAACAAATAT  TGGAGTGAAG
TTGTTGCATA  ACTTGCATCG  AACAATTAAT  AGAAATAACA  GAAAATTAAA
AAAGAAATAT  G,
```

Lbc₁ with the sequence:

```
TTCTCTTAAT  ACAATGGAGT  TTTTGTTGAA  CATACATACA  TTTAAAAAAA
AATCTCTAGT  GTCTATTTAC  CCGGTGAGAA  GCCTTCTCGT  GTTTTACACA
CTTTAATATT  ATTATATCCT  CAACCCCACA  AAAAAGAATA  CTGTTATATC
TTTCCAAACC  TGTAGATTTA  TTTATTTATT  TATTTATTTT  TACAAAGGAG
ACTTCAGAAA  AGTAATTACA  TAAAGATAGT  GAACATCATT  TTATTTATTA
TAATAAACTT  TAAAATCAAA  CTTTTTTATA  TTTTTTGTTA  CCCTTTTCAT
TATTGGGTGA  AATCTCATAG  TGAAGCCATT  AAATAATTTG  GGCTCAAGTT
TTATTAGTAA  AGTCTGCATG  AAATTTAACT  TAACAATAGA  GAGAGTTTTC
GAAAGGGAGC  GAATGTTAAA  AAGTGTGATA  TTATATTTTA  TTTCGATTAA
TAATTATGTT  TACATGAAAA  CATACAAAAA  AATACTTTTA  AATTCAGAAT
AATACTTAAA  ATATTTATTT  GCTTAATTGA  TTAACTGAAA  ATTATTTGAT
TAGGATTTTG  AAAAGATCAT  TGGCTCTTCG  TCATGCCGAT  TGACACCCTC
CACAAGCCAA  GAGAAACTTA  AGTTGTAAAC  TTTCTCACTC  CAAGCCTTCT
ATATAAACAT  GTATTGGATG  TGAAGTTATT  GCATAACTTG  CATTGAACAA
TAGAAAATAA  CAAAAAAAAG  TAAAAAAGTA  GAAAAGAAAT  ATG,
```

Lbc₂ with the sequence:

```
TCGAGTTTTT  ACTGAACATA  CATTTATTAA  AAAAAACTCT  CTAGTGTCCA
TTTATTCGGC  GAGAAGCCTT  CTCGTGCTTT  ACACACTTTA  ATATTATTAT
ATCCCCACCC  CCACCAAAAA  AAAAAAAACT  GTTATATCTT  TCCAGTACAT
TTATTTCTTA  TTTTTACAAA  GGAAACTTCA  CGAAAGTAAT  TACAAAAAAG
ATAGTGAACA  TCATTTTTTT  AGTTAAGATG  AATTTTAAAA  TCACACTTTT
TTATATTTTT  TTGTTACCCT  TTTCATTATT  GGGTGAAATC  TCATAGTGAA
ACTATTAAAT  AGTTTGGGCT  CAAGTTTTAT  TAGTAAAGTC  TGCATGAAAT
TTAACTTAAT  AATAGAGAGA  GTTTTGGAAA  GGTAACGAAT  GTTAGAAAGT
GTGATATTAT  TATAGTTTTA  TTTAGATTAA  TAATTATGTT  TACATGAAAA
TTGACAATTT  ATTTTTAAAA  TTCAGAGTAA  TACTTAAATT  ACTTATTTAC
TTTAAGATTT  TGAAAAGATC  ATTTGGCTCT  TCATCATGCC  GATTGACACC
CTCCACAAGC  CAAGAGAAAC  TTAAGTTGTA  ATTTTTCTAA  CTCCAAGCCT
TCTATATAAA  CACGTATTGG  ATGTGAAGTT  GTTGCATAAC  TTGCATTGAA
CAATAGAAAT  AACAACAAAG  AAAATAAGTG  AAAAAAGAAA  TATG,
```

Lbc₃ with the sequence:

```
TATGAAGATT  AAAAAATACA  CTCATATATA  TGCCATAAGA  ACCAACAAAA
GTACTATTTA  AGAAAAGAAA  AAAAAAACCT  GCTACATAAT  TTCCAATCTT
GTAGATTTAT  TTCTTTTATT  TTTATAAAGG  AGAGTTAAAA  AAATTACAAA
ATAAAAATAG  TGAACATCGT  CTAAGCATTT  TTATATAAGA  TGAATTTTAA
AAATATAATT  TTTTTGTCTA  AATCGTATGT  ATCTTGTCTT  AGAGCCATTT
TTGTTTAAAT  TGGATAAGAT  CACACTATAA  AGTTCTTCCT  CCGAGTTTGA
TATAAAAAAA  ATTGTTTCCC  TTTTGATTAT  TGGATAAAAT  CTCGTAGTGA
CATTATATTA  AAAAAATTAG  GGCTCAATTT  TTATTAGTAT  AGTTTGCATA
AATTTTAACT  TAAAAATAGA  GAAAATCTGG  AAAAGGGACT  GTTAAAAAGT
GTGATATTAG  AAATTTGTCG  GATATATTAA  TATTTTATTT  TATATGGAAA
CTAAAAAAAT  ATATATTAAA  ATTTTAAATT  CAGAATAATA  CTTAAATTAT
TTATTTACTG  AAAATGAGTT  GATTTAAGTT  TTTGAAAAGA  TGATTGTCTC
TTCACCATAC  CAATTGATCA  CCCTCCTCCA  ACAAGCCAAG  AGAGACATAA
GTTTTATTAG  TTATTCTGAT  CACTCTTCAA  GCCTTCTATA  TAAATAAGTA
TTGGATGTGA  AGTTGTTGCA  TAACTTGCAT  TGAACAATTA  ATAGAAATAA
CAGAAAAGTA  GAAAAGAAAT  ATG.
```

The invention relates furthermore to any plasmid to be used when carrying out the method according to the invention and characterised by comprising a DNA fragment containing an inducible plant promoter as herein defined. Suitable plasmids according to the invention are pAR11, pAR29, and pAR30, cf. Examples 3 and 4, which furthermore allows recombination into the *A. rhizogenes* T DNA region.

The invention relates furthermore to any Agrobacterium strain to be used in connection with the invention and characterised by comprising a DNA fragment comprising an inducible plant promoter of root nodule-specific genes built into the T DNA region and therefore capable of transforming the inducible promoter into plants. Bacterium strains according to the invention are the *A. rhizogenes* strains AR1127, AR1134 carrying Lbc₃ 5' 3'-CAT, and AR1000 carrying the Lbc₃ gene.

It is obvious that the patent protection of the present invention is not limited by the embodiments stated above.

Thus the invention employs not exclusively 5' flanking regions of soybean leghemoglobin genes. It is well-known that the leghemoglobin genes of all leguminous plants have the same function, cf. Appleby (1974) in The Biology of Nitrogen Fixation, Quispel. A. Ed. North-Holland Publishing Company, Amsterdam, Oxford, pages 499–554, and concerning the kidney bean PvLb1 gene it has furthermore been proved that a high degree of homology exists with the sequences of the soybean Lbc₃ gene. It is also known that the expression of other root nodule-specific genes is regulated in a similar manner like the leghemoglobin genes. The invention includes thus the use of 5' flanking regions of leghemoglobin genes or other root nodule-specific genes of all plants in case the use of such DNA fragments makes the expression of a desired gene product the subject matter of the regulation characterised by the present invention.

The present invention allows also the use of such fragments of any origin which under natural conditions exert or mediate the regulation characterised by the present invention. The latter applies especially to such fragments which can be isolated from DNA fragments from gene libraries or genomes through hybridization with marked sequences of 5' flanking regions of soybean leghemoglobin genes.

It is well-known that it is possible to alter nucleotide sequences of non-important sub-regions of 5' flanking regions without causing an alteration of the promoter activity and the regularity. It is also well-known that an alteration of sequences of important subregions of 5' flanking regions renders it possible to alter the binding affinities between nucleotide sequences and the factors or effector substances necessary for the transcription initiation and the translation initiation and consequently to improve the promoter activity and/or the regularity. The present invention includes, of course, also the use of DNA fragments containing such altered sequences of 5' flanking regions, and in particular DNA fragments can be mentioned which have been produced by recombining regions of 5' flanking regions of any gene with 5' flanking regions of root nodule-specific genes provided the use of such DNA fragments subjects the expression of a desired gene product of the regulation characterised by the present invention.

It should be noted that the transformation of microorganisms is carried out in the manner known per se, cf. e.g. Maniatis et al., (1982), Molecular Cloning, Cold Spring Harbor Laboratory.

The transformation of plant cells, i.e., introduction of plasmid DNA into plant cells, is also carried out in a manner known per se, cf. Zambryski et al., (1983), EMBO J. 2, 2143–2150.

Cleavage with restriction endonucleases and digestion with other DNA modified enzymes are well-known techniques and are carried out as recommended by the suppliers.

The *Agrobacterium rhizogenes* 15834 rif$^R$ used in connection with the present invention has been isolated by J. A. Lippincott, Department of Biological Sciences, Northwest University, Evanston, Ill. 60201, USA.

BRIEF DESCRIPTION OF THE DRAWINGS

FIGS. 1A & 1B shows four 5' flanking regions of soybean leghemoglobin genes.

FIG. 7 shows a scheme for cloning and integrating the soybean Lbc₃ gene.

Figure 8A:
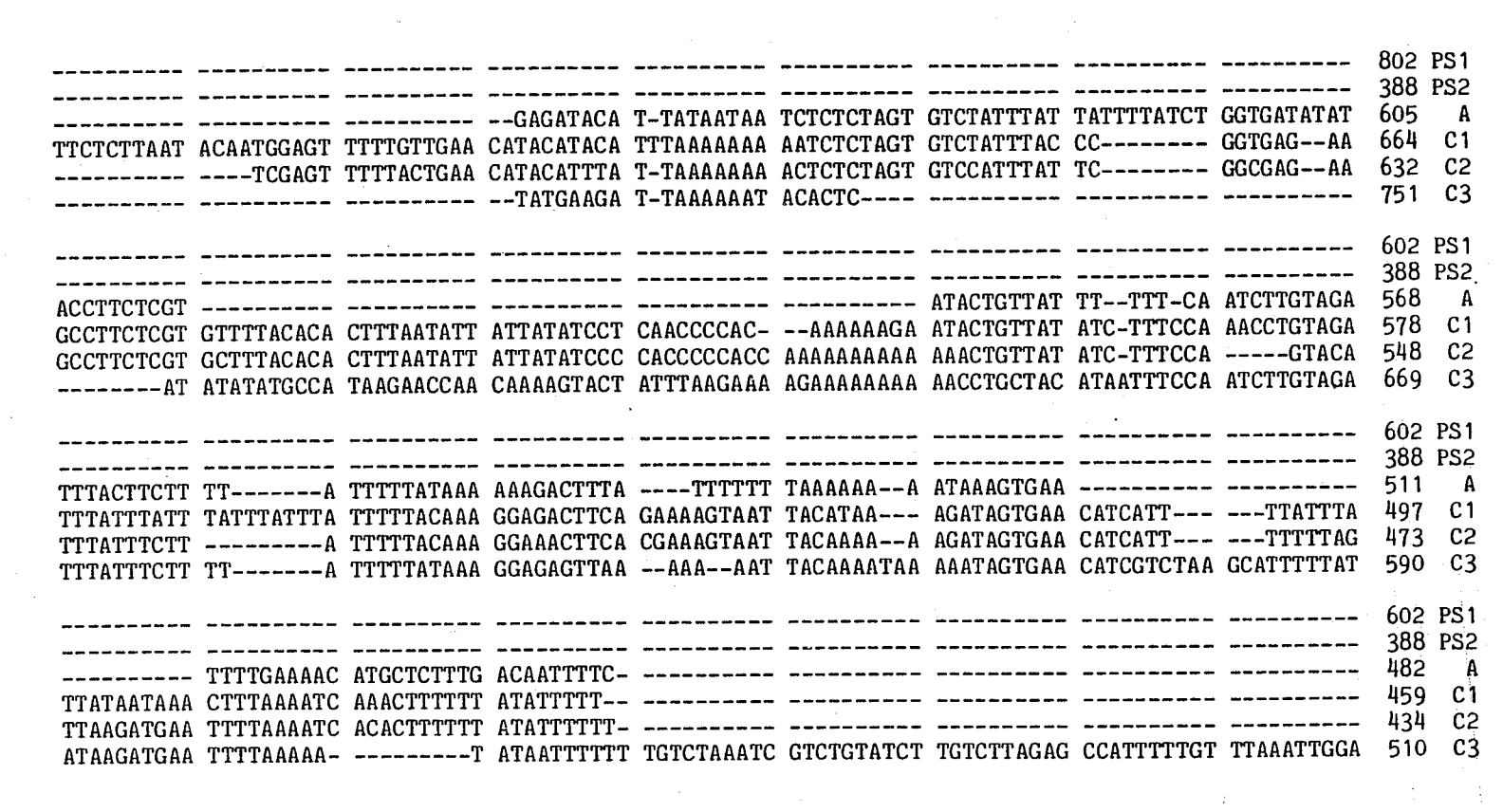
Figure 8B:
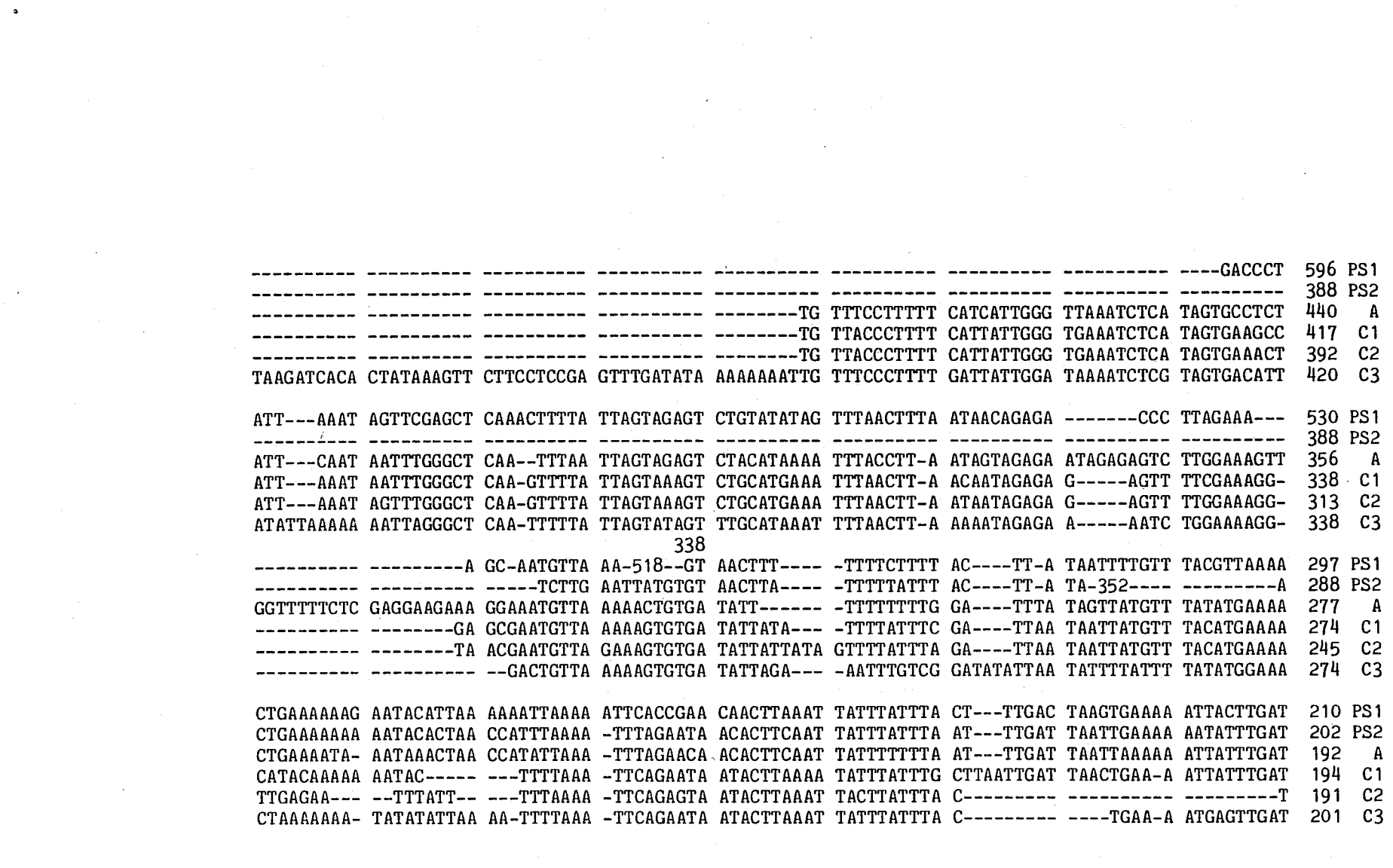

FIGS. 8A, B & C shows alignment of the 5' end sequences of the Lb genes. At the right is seen the name of the gene and the base number counted upstream from ATG. A dash means no base was present. The gaps are created to make the best alignment between the different 5' ends.

EXAMPLE 1

Sequence determination of 5' flanking regions of soybean leghemoglobin genes From a soybean gene library the four soybean leghemoglobin genes Lba, Lbc$_1$, Lbc$_2$, and Lbc$_3$ are provided as described by Jensen, E. O. et al., Nature Vol. 291, No. 3817, 677–679 (1981). The 5' flanking regions of the four soybean leghemoglobin genes are isolated, as described by Jensen, E. O., Ph D Thesis, Institut for Molekylaer Biologi, Århus Universitet (1985), and the sequences of the four 5' flanking regions are determined by the use of the dideoxy method as described by Sanger, F., J. Mol. Bio. 143, 161 (1980) and indicated in FIG. 1.

EXAMPLE 2

Construction of Lbc$_3$-5'-3' CAT

The construction has been carried out in a sequence of process sections as described below:

Sub-cloning the Lbc$_3$ gene

Figure 2:
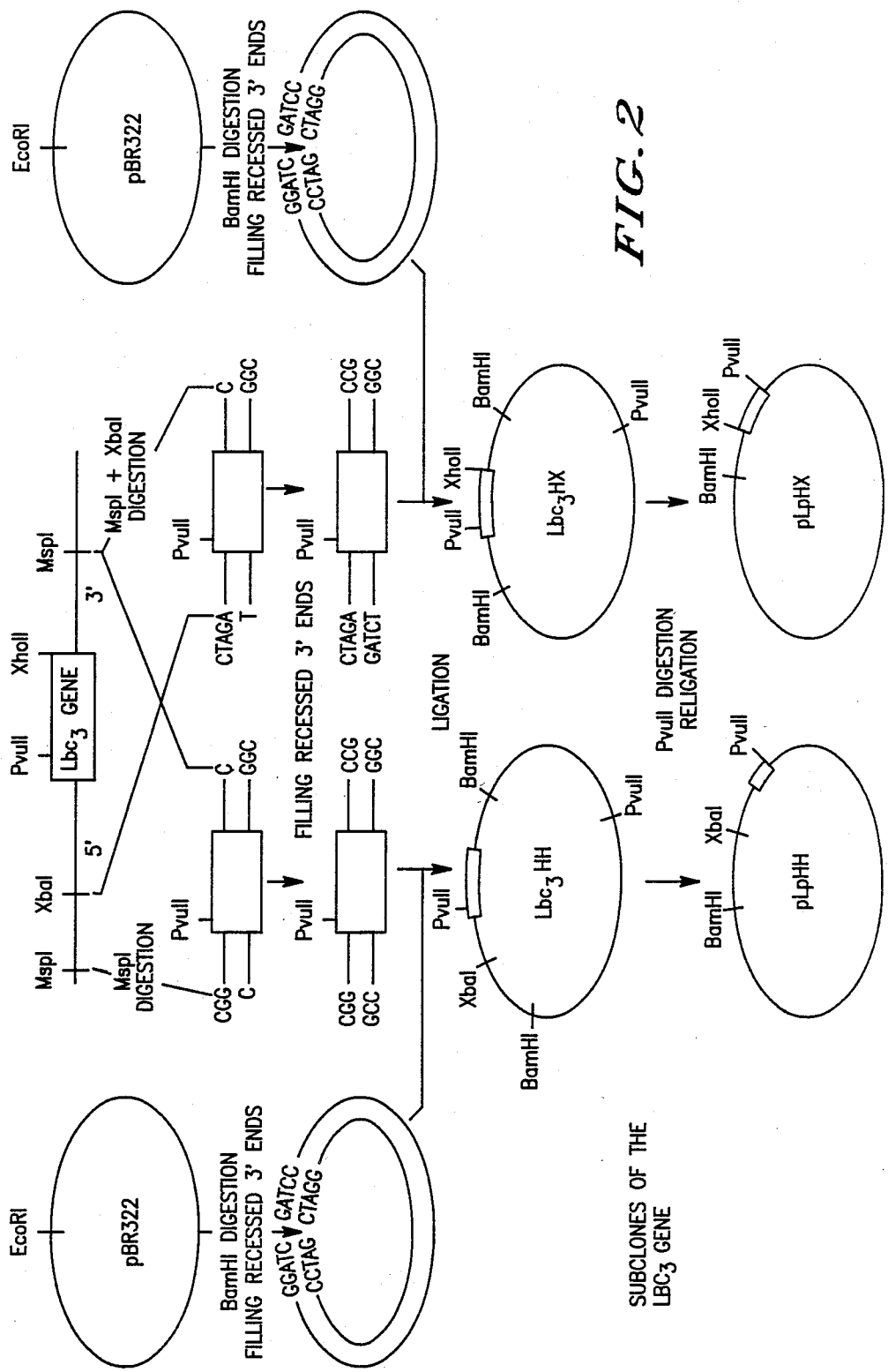
FIG. 2 shows subclones of the Lbc₃ gene.

The Lbc$_3$ gene was isolated on a 12Kb EcoRI restriction fragment from a soybean DNA library, which has been described Wy Wiborg et al., in Nucl. Acids Res. (1982) 10, 3487. A section of the fragment is shown at the top of FIG. 2. This fragment was digested by the enzymes stated and then ligated to pBR322 as indicated in FIG. 2. The resulting plasmids Lbc$_3$HH and Lbc$_3$HX were subsequently digested by PvuII and religated, which resulted in two plasmids called pLpHH and pLpHx.

Sub-cloning 5' flanking sequences from the Lbc$_3$ gene

Figure 3:
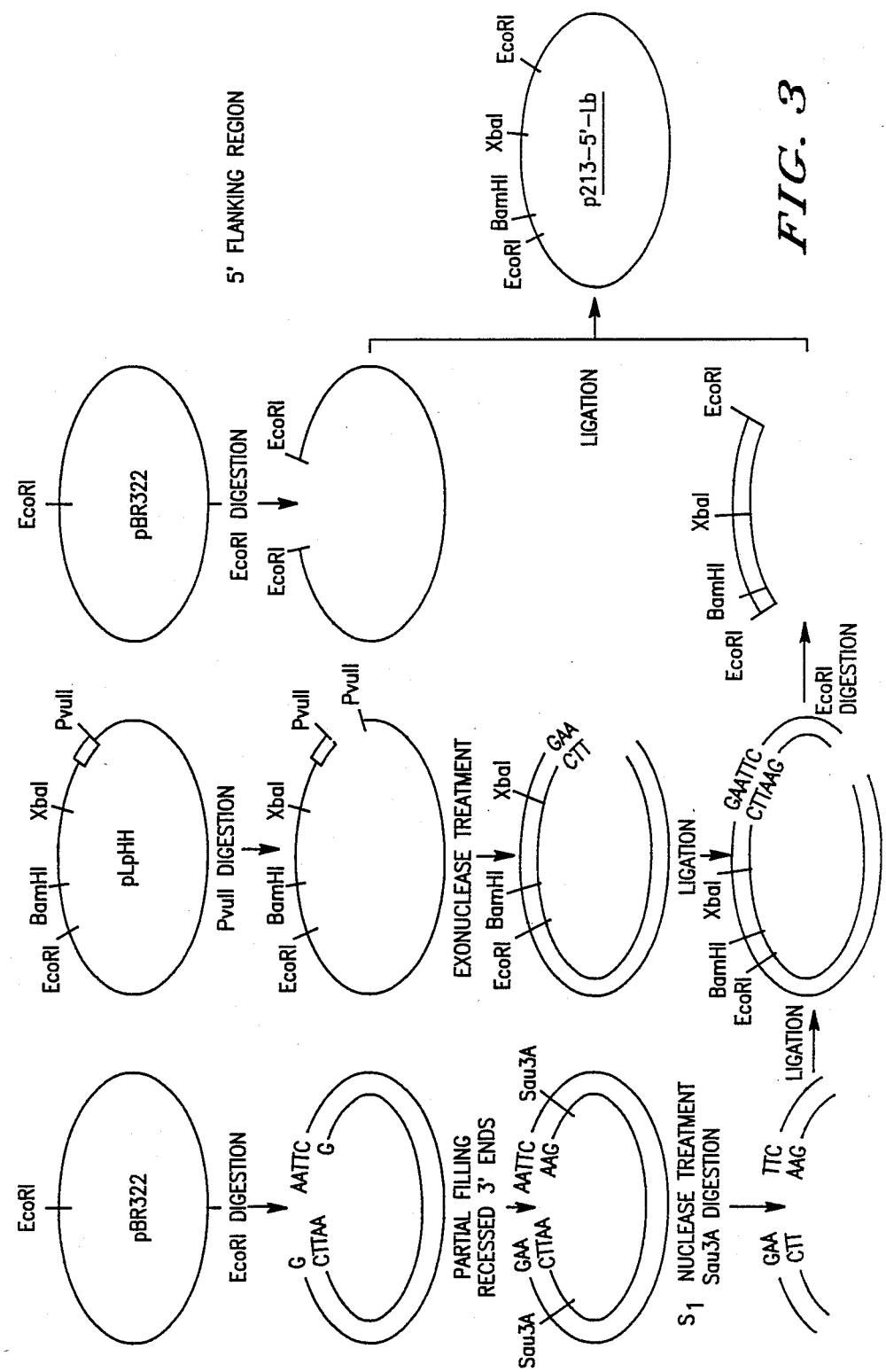
FIG. 3 shows subcloning of the 5' flanking sequences from the Lbc₃ gene.

For this purpose pLpHH was used as shown in FIG. 3. This plasmid was opened by means of PvuII and treated with exonuclease Bal31. The reaction was stopped at various times and the shortened plasmids were ligated into fragments from pBR322. These fragments had been treated in advance as shown in FIG. 3, in such a manner that in one end they had a DNA sequence

```
TTC ---
AAG ---.
```

After the ligation a digestion with EcorRI took place, and the fragments containing 5' flanking sequences were ligated into EcoRI digested pBR322. These plasmids were transformed into *E. coli* K803, and the plasmids in the transformants were tested by sequence analysis. A plasmid, p213 5'Lb, isolated from one of the transformants, contained a 5' flanking sequence terminating 7 bp before the Lb ATG start codon in such a manner that the sequence is as follows:

```
                  2Kb
          -5' flanking - AAAGTAGAATTC
             Lbc3 sequence
```

Sub-cloning 3' flanking region of the Lbc$_3$ gene

Figure 4:
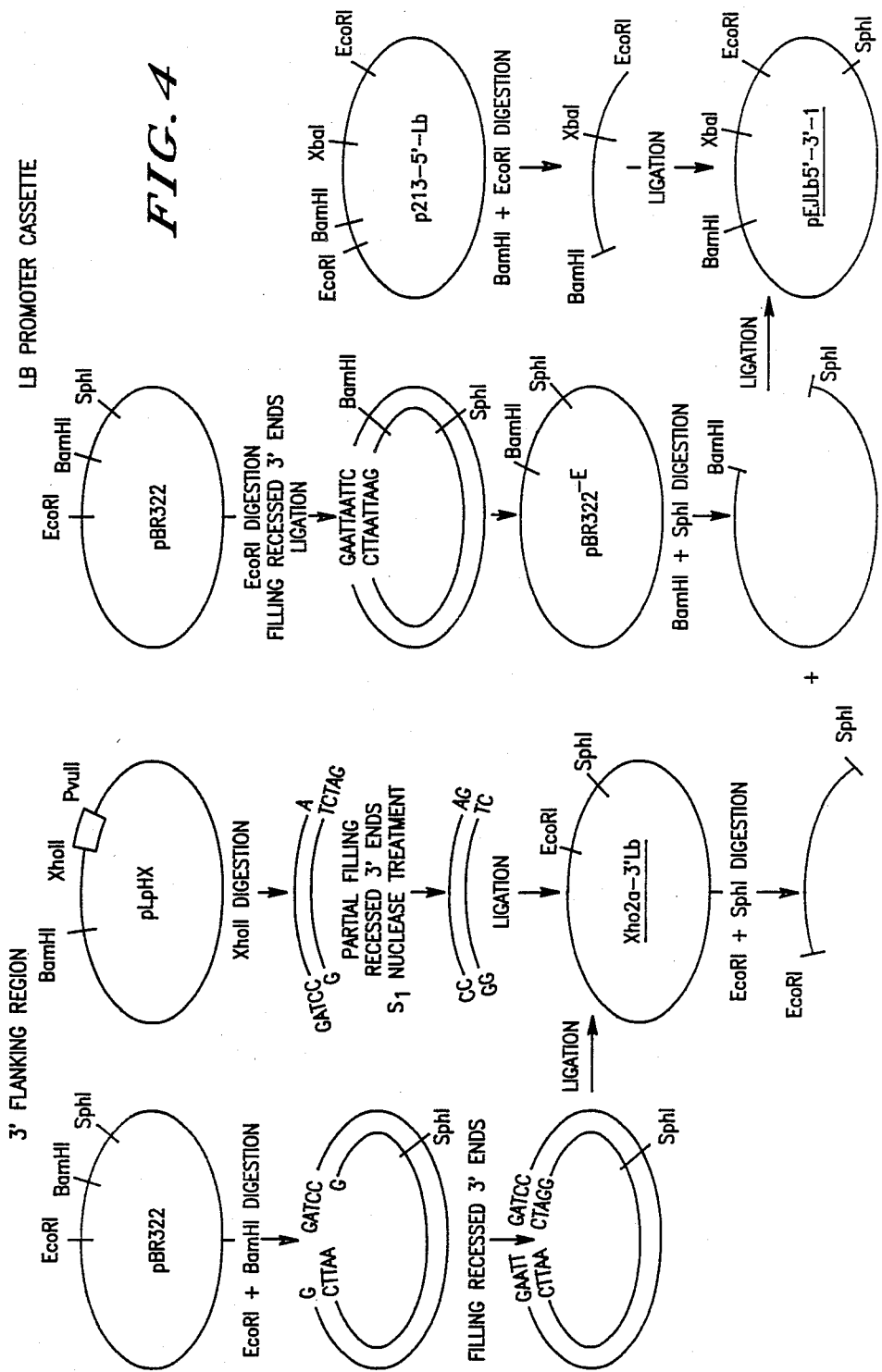
FIG. 4 shows a scheme for subcloning the 3' flanking region of the Lbc₃ gene.

For this purpose pLpHx was used which was digested by XhoII. The ends were partially filled out and excess DNA was removed, as shown in FIG. 4. The fragment shown was ligated into pBR322 which has been pretreated as shown in FIG. 4. The construction was transformed into *E. coli* K803. One of the transformants contained a plasmid called Xho2a-3'Lb. As the XhoII recognition sequence is positioned immediately after the Lb stop codon, cf. FIG. 2, the plasmid contained about 900 bp of the 3' flanking region, and the sequence started with GAATTCTACAA - - - .

The construction of Lb promoter cassette

An EcoRI/SphI fragment from Xho2a-3'Lb was mixed with a BamHI/EcoRI fragment from p213-5'Lb. These two fragments were ligated via the BamHI/SphI cleavage sites into a pBR322 derivative where the EcoRI recognition sequence had been removed, cf. FIG. 4. The ligated plasmids were transformed into *E. coli* K803. A plasmid in one of the transformants contained the correct fragments, and it was called pEJLb 5'-3'-1.

Construction of chimeric Lb/CAT gene

Figure 5:
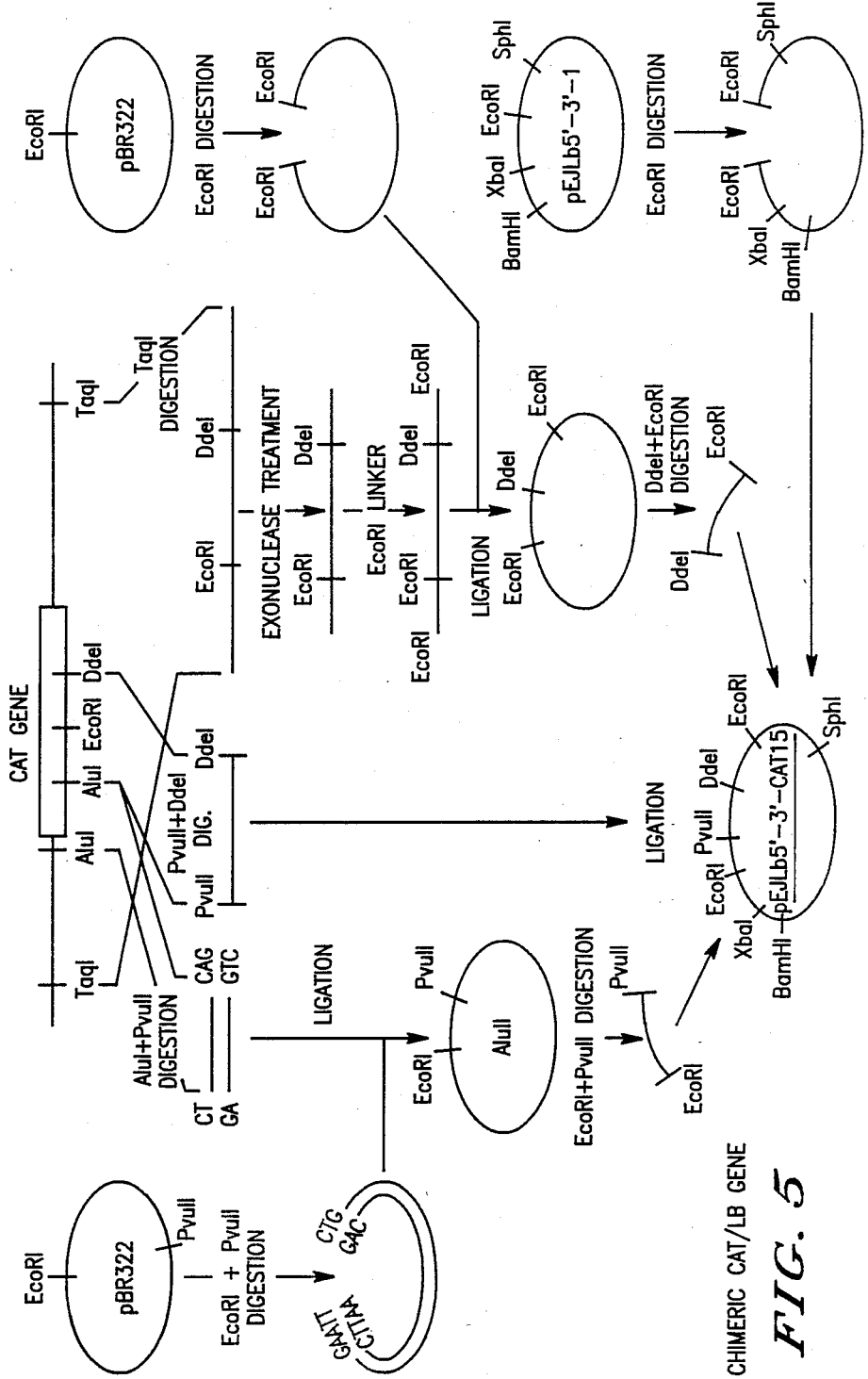
FIG. 5 shows construction of the chimeric Lb/CAT gene.

The CAT gene of pBR322 was isolated on several smaller restriction fragments, as shown in FIG. 5. The 5' coding region was isolated on an AluI fragment which was subsequently ligated into pBR322, treated as stated in FIG. 5. This was transformed into *E. coli* K803, and a selected transformant contained a plasmid called AluI. The 3' coding region was isolated on a Taq1 fragment. This fragment was treated with exonuclease Bal31, whereafter EcoRI linkers were added. Then followed a digestion with EcoRI and a ligation to EcoRI digested pBR322. The latter was transformed into *E. coli* K803 and the transformants were analysed. A plasmid, Taq 12, contained the 3' coding region of the CAT gene plus 23 bp 3' flanking sequences subsequently terminating in the following sequence CCCCAATTC. Subsequently the following fragments were ligated together to EcoRI digested pEJLb5'-3'-1: EcoRI/PvuII fragment from AluI, PvuII/DdeI fragment from pBR322 and DdeI/EcoRI fragment from Taq 12. The latter was transformed into *E. coli* K803. A selected transformant contained the correct plasmid and was called pEJLb 5'-3' CAT 15.

EXAMPLE 3 a.

Cloning and integration of the soybean Lbc$_3$-5'-3' CAT gene

Figure 6:
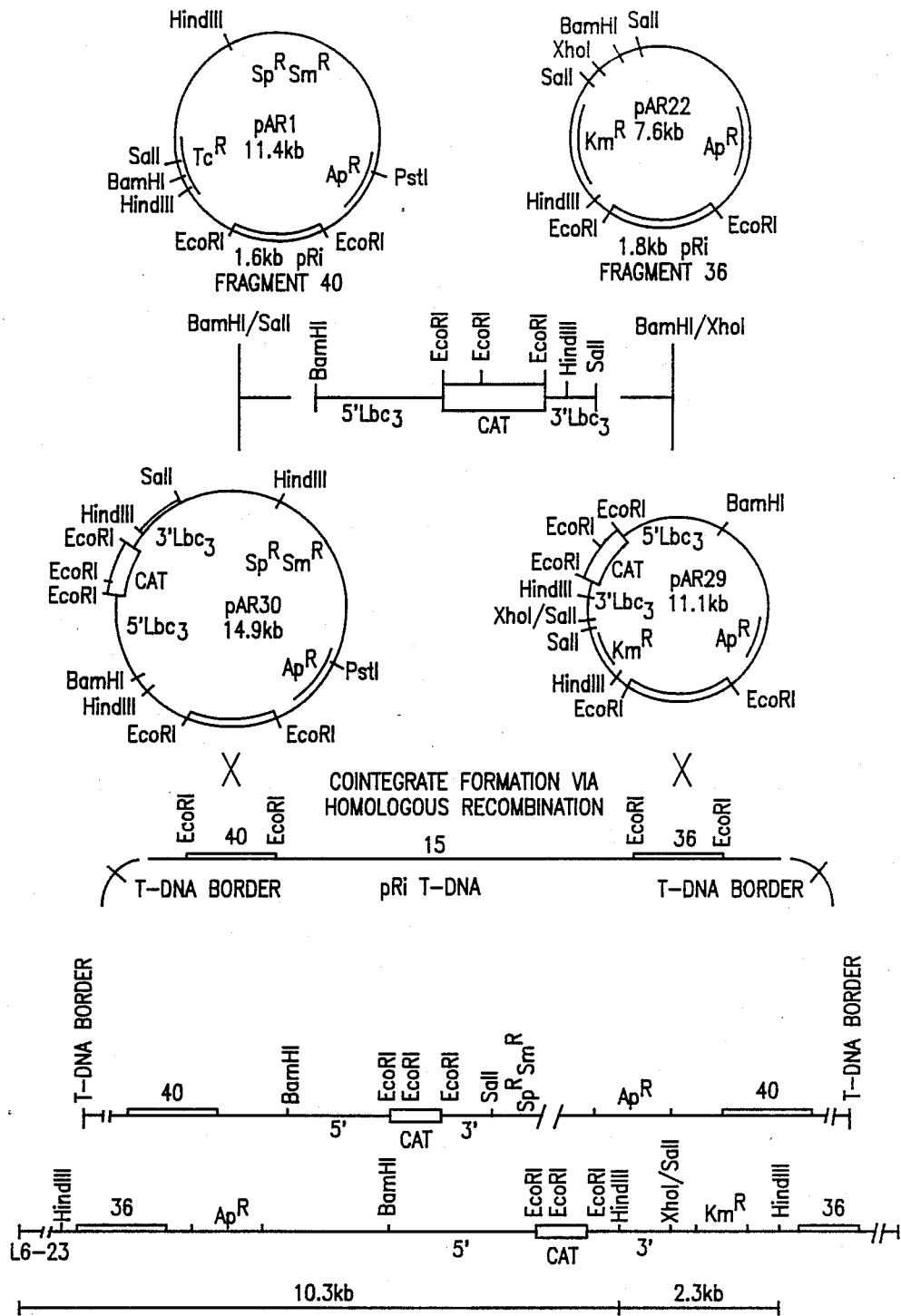
FIG. 6 shows the structure of T₁ DNA regions transferred to transformed plant lines.

Two EcoRI fragments (No. 36 and No. 40) of the T$_L$ DNA region of A. rhizogenes 15834 pRi plasmid was used as "integration sites". Thus the Lbc$_3$ 5' 3' CAT gene was subcloned (as 3,6 Kb BamHI/SalI fragment) into two vectors pAR1 and pAR22 carrying the above EcoRI fragments. The resulting plasmids pAR29 and pAR30 were subsequently mobilized into A. rhizogenes 15834 rif$^R$. Neither pAR29 nor pAR30 can replicate in Agrobacterium. Therefore the selection by means of rifampicin 100 μg/ml and the plasmid markers spectinomycine 100 μg/ml, streptomycine 100 μg/ml or kanamycine 300 μg/ml will select A. rhizogenes bacteria having integrated the plasmids via homologous recombination through the EcoRI fragments 36 or 40. The structure of the resulting T$_L$ DNA regions—transferred to the transformed plant lines L5-9 and L6-23—has been indicated at the bottom of FIG. 6. In addition to the L6-23 line, there is also shown in FIG. 7 and the EcoRI and HindIII fragments carrying the Lbc$_3$ 5' 3' CAT gene and therefore hybridizing to radioactively marked Lbc$_3$ 5' 3' CAT DNA, cf. Example 4a (see FIG. 9).

b.

Cloning and integration of the soybean Lbc$_3$ gene

Figure 10:
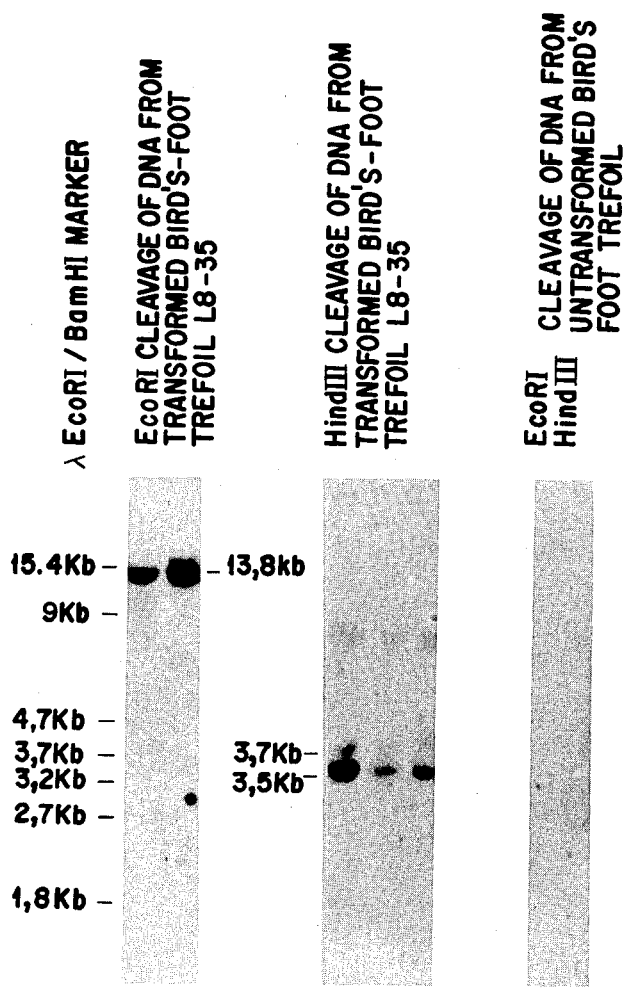
FIG. 10 corresponds to Example 4b. and shows a demonstration of the soybean Lbc$_3$ gene of transformed plants of bird's-foot trefoil.

The EcoRI fragment No. 40 has here been used as "integration site". The Lbc$_3$ gene was therefore subcloned (as a 3,6 Kb BamHI fragment into the pAR1 vector and transferred into the T$_L$ DNA region as stated in a. The structure of the T$_L$ DNA region, transferred to the transformed plant line L8-35, has been shown at the bottom of FIG. 7. FIG. 7 furthermore shows the EcoRI and HindIII fragments carrying the Lbc$_3$ gene and therefore hybridizing with radioactively marked Lbc$_3$ DNA, cf. Example 4b [see FIG. 10].

Figure 9:
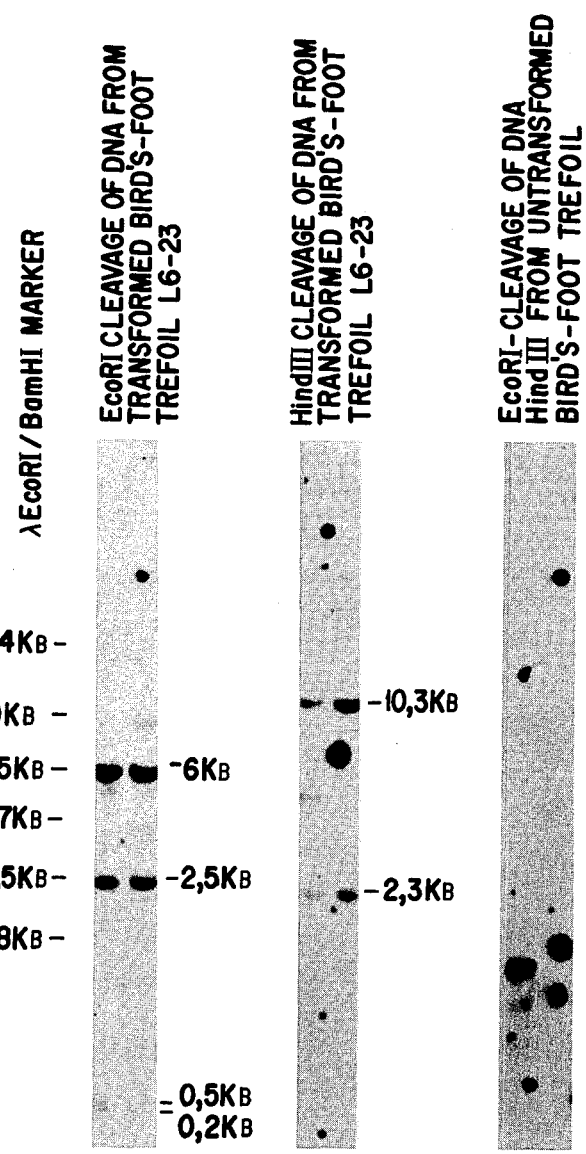
FIG. 9 corresponds to Example 4a. and shows a demonstration of the soybean Lbc$_3$ 5' 3' CAT gene in transformed plants of bird's-foot trefoil.

EXAMPLE 4 a. [see FIG. 9] -

DNA extracted from transformed lines (L6-23) or untransformed control plants and cleaved by the restriction enzymes EcoRI and HindIII was analyzed by Southern-hybridization. Radioactive Lbc$_3$ 5' 3' CAT gene was used for demonstrating corresponding sequences in the transformed lines. The bands marked with numbers correspond to restriction fragments constituting parts of the Lbc$_3$ 5' 3' CAT gene as stated in the restriction map (FIG. 6) of Example 3a.

EXAMPLE 4b. (see FIG. 10)

DNA extracted from transformed lines (L8-35) or untransformed control plants and cleaved by the restriction enzymes EcoRI and HindIII was analyzed by Southern-hybridization. Radioactive Lbc$_3$ gene was used for detecting corresponding sequences in the transformed lines. The bands marked with numbers correspond to restriction fragments constituting parts of the Lbc$_3$ gene as stated in the restriction map (FIG. 7) of Example 3b.

Figure 11:
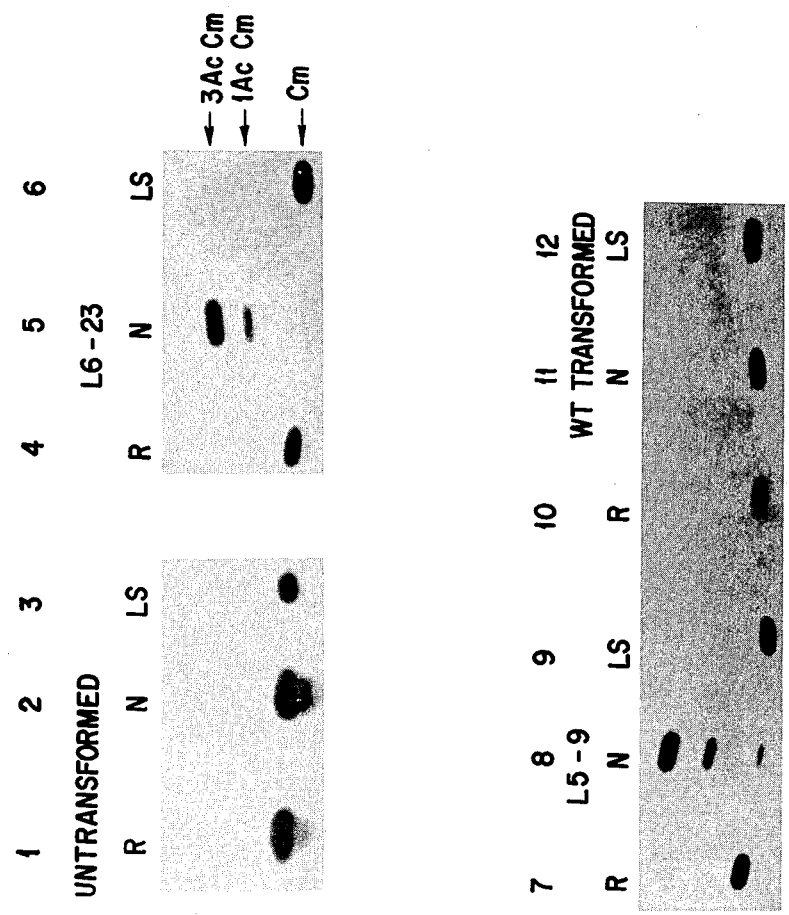
FIG. 11 corresponds to Example 5a and shows tissue specific expression of the soybean Lbc$_3$ 5' 3' CAT gene in root nodules of bird's-foot trefoil.

EXAMPLE 5 (see FIG. 11)

a.

The activity of the chloroamphenicol acetyl transferase (CAT) enzyme is measured as the amount of acetylated chloroamphenicol (AcCm) produced from $^{14}$C-chloroamphenicol. In (a) FIG. 11, the acetylated forms 1AcCm and 3AcCm appear, which have been separated from Cm through thin-layer chromatography in chloroform/methanol (95:5). The columns 1–3 show that no CAT activity occurs in root (R), nodule (N), as well as leaves+stem (LS) of untransformed plants of bird's-foot trefoil. The columns 4–6 and 7–9 show the CATA activity in corresponding tissues of Lbc$_3$ 5' 3' CAT transformed L6-23 and L5-9 plants. The conversion of chloroamphenicol in columns 5 and 8 shows the tissue-specific expression of the Lbc$_3$ 5' 3' CAT gene in root nodules. The columns 10–12 show the lack of CAT activity in plants transformed by means of wild type A. rhizogenes.

EXAMPLE 5 b.

TABLE

|  | L6-23 CAT activity | L5-9 CAT activity |
| --- | --- | --- |
| Root | 0 | 0 |
| Nodule | 68830 cpm/μg protein · hour | 154,000 cpm/μg protein · hour |
| Leaves + Stem | 0 | 0 |

In the Table (b) the CAT activity in Lbc$_3$ 5' 3' CAT transformed L5-9 and L6-23 plants has been stated as the amount of $^{14}$C-chloroamphenicol converted into acetylated derivatives. The amount of radioactivity in the acetylated derivatives has been counted by liquid scintillation and stated in cpm/μg protein·hour.

Figure 12:
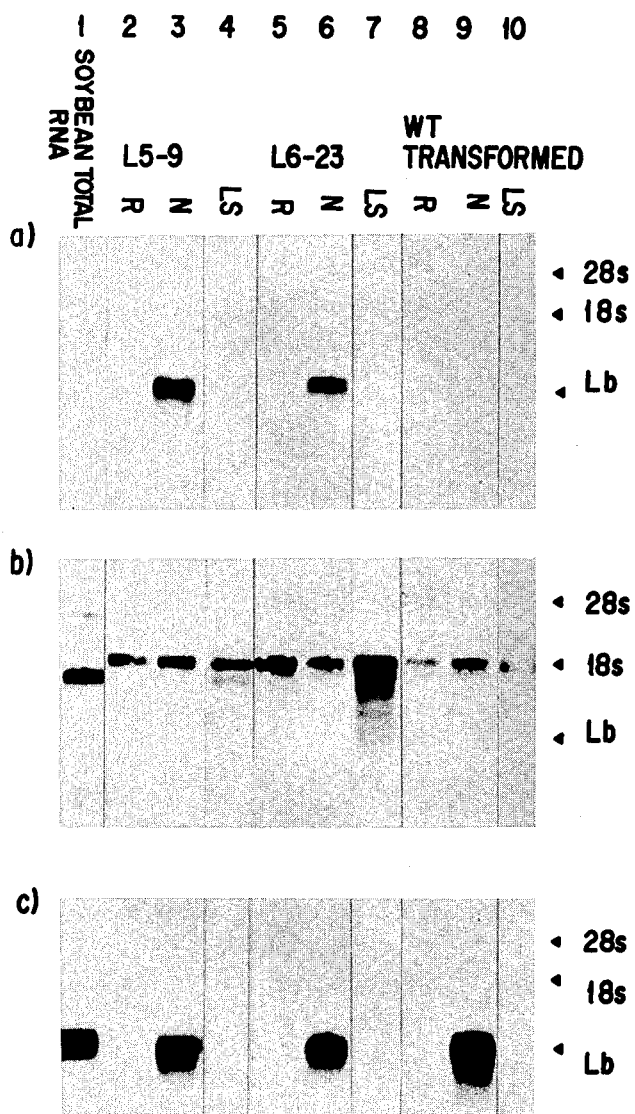
FIGS. 12A, B & C corresponds to Example 6 and shows a transcription test on tissues of Lbc$_3$ 5' 3' transformed and wild type *A. rhizogenes* bird's-foot trefoil plant lines.

EXAMPLE 6 (see FIG. 12)

5 μg of total RNA extracted from root (R), nodule (N) or leaves+stem (LS) and separated in formaldehyde agarose gels were transferred onto nitrocellulose. Column 1 contains 5μ of total RNA from soybean control plants. The columns 2–4 and 5–7 contains total RNA from root, nodule or leaves+stem, respectively, of the Lbc$_3$ 5' 3' CAT transformed lines L5-9 and L6-23. The columns 8–10 contain RNA from corresponding tissues of bird's-foot trefoil transformed by means of the wild type A. rhizogenes. In (a) radioactive DNA of the CAT coding sequence has been used for hybridization. The tissue-specific transcription of the Lbc$_3$ 5' 3' CAT gene in root nodules from the L5-9 and L6-23 lines appears from columns 3 and 6. In (b) the constitutive expression of the ubiquitine genes appears. A human cDNA is used for the hybridization. In (c) the tissue-specific expression of bird's-foot trefoil own leghemoglobin genes is shown. A cDNA of the Lba gene of soybean has been used for this hybridization.

Figure 13:
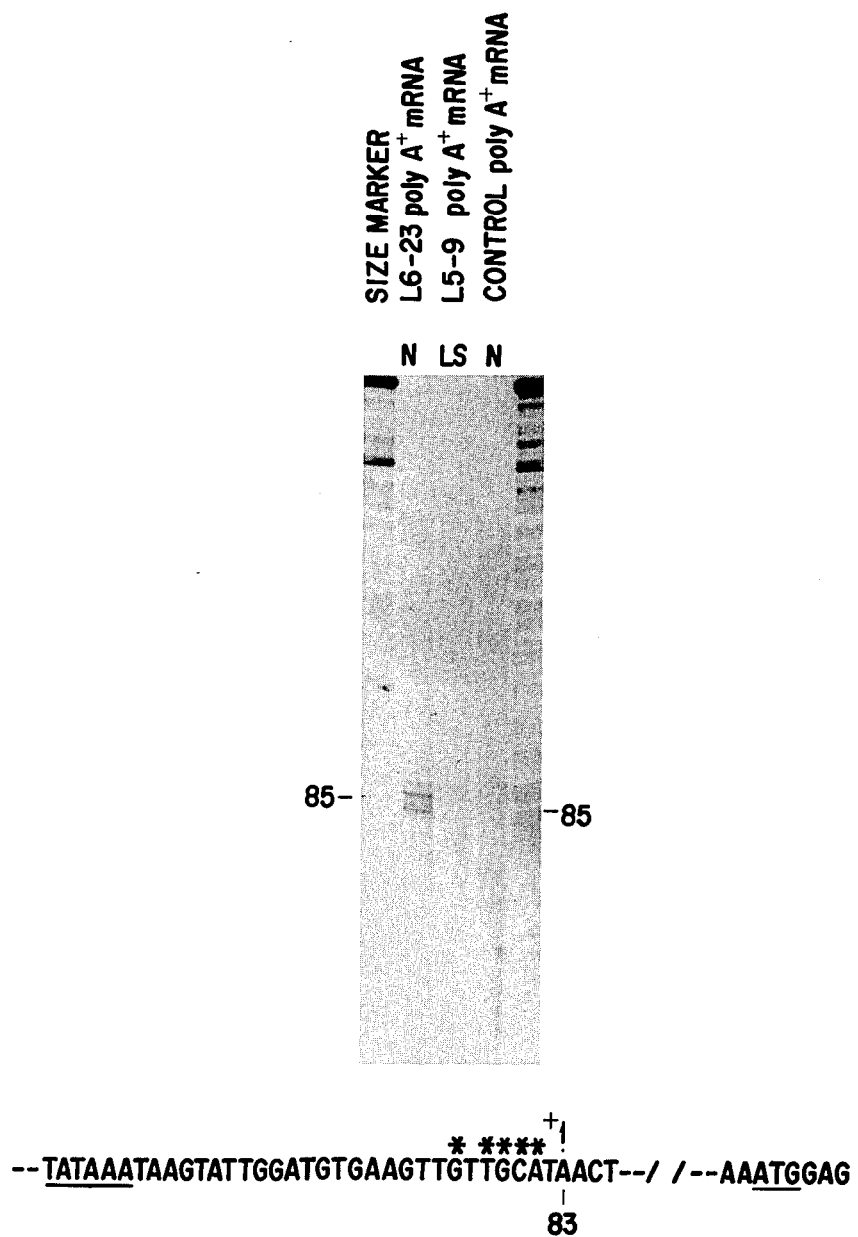
FIG. 13 corresponds to Example 7 and shows a determination of the transcription initiation site (CAP site) of the Lbc$_3$ promoter of soybean in transformed root nodules of bird's-foot trefoil.

EXAMPLE 7 (see FIG. 13)

The position of the "CAP site" was determined on the nucleotide level by means of primer extension. A short oligonucleotide corresponding to the nucleotides 15–34 in the coding sequence of the CAT gene was used as primer for the enzyme reverse transcriptase. As a result single-stranded DNA was formed the length of which corresponds to the distance between the 5' end of the primer and the 5' end of the primed mRNA. A 83 nucleotide DNA strand is expected according to the knowledge of the transcription initiation site of soybean. Columns 2, 3, and 4 from left to right show the produced DNA strands when the primer extension has been operated on polyA+-purified mRNA from transformed root nodules of bird's foot trefoil, transformed leaves+stem of bird's-foot trefoil, and untransformed root nodules of bird's-foot trefoil, respectively. The 85, 86, 87, 88, and 90 nucleotides long DNA strand shown in column 2 proved correctly $Lbc_3$ promoter function in bird's-foot trefoil. On the inserted DNA sequence the nucleotides to which the 7-methyl GTP is added ("CAP site") in bird's-foot trefoil are marked by (*). On the nucleotide in position +1 the 7-methyl GTP is added in soybean. In the sequence the TATAA box of the $Lbc_3$ promoter and the corresponding translation initiation codon is marked by an underlining.

EXAMPLE 8

Demonstration of the correct developing control of the $Lbc_3$ 5' 3' CAT gene in transformed plants of bird's-foot trefoil (L6-23).

the 5' flanking regions comprising the promoter are controlled by the tissue-specific regulatory mechanism as the tissue-specific control of the chimeric $Lbc_3$ gene in *Lotus corniculatus* took place at the transcription level. The chimeric $Lbc_3$ gene transferred was thus only transcribed in root nodules on transformed plants and not in other tissues such as roots, stems, and leaves.

The expression of the chimeric $Lbc_3$ gene in root nodules of transformed plants also followed the developmental timing known from soybean root nodules. No CAT activity could be detected in roots or small white root nodules (Example 8). A low activity was present in the further developed white distinct nodules, whereas a high activity could be measured in the small red nodules and mature nodules developed latter on.

The tissue-specific expression and the correct developmental expression of transferred root nodule-specific genes, here exemplified by the chimeric $Lbc_3$ gene, allows as a particular use a functional expression of root nodule-specific genes also in other plants beyond leguminous plants. When all the root nodule-specific plant genes necessary for the formation of root nodules are transferred from a leguminous plant to a non-root-nodule-forming plant species, the correct tissue-specific

|  | Stage 1: No visible nodules | Stage 2: Imerging nodules | Stage 3: Distinct white nodules | Stage 4: Small pink nodules | Stage 5: Later stage of maturity |
|---|---|---|---|---|---|
| CAT activity in cmp/μg protein · hour | 0 | 0 | 32.6 | 342.3 | 1255* |
| Nitrogenase activity nmol ethylene/μg protein hour | 0 | 0 | 0 | 0.5 | 2.7 |

*Substrate restricted, actual activity about 68000 cpm/μg protein · hour.

Chloroamphenicol acetyl transferase and nitrogenase activity were measured on cut off pieces of root with root nodules at the stages of development indicated. The CAT activity can be detected in the white distinct nodules whereas the nitrogenase activity did not appear until the small red nodules have developed. The latter development corresponds to the development known from soybean control plants and documented in Marcker et al. EMBO J. 1984, 3, 1691-95. The CAT activity was determined as in Example 5. The nitrogenase activity was measured as acetylene reduction followed by gas chromatographic determination of ethylene.

EXAMPLE 9

Figure 14:
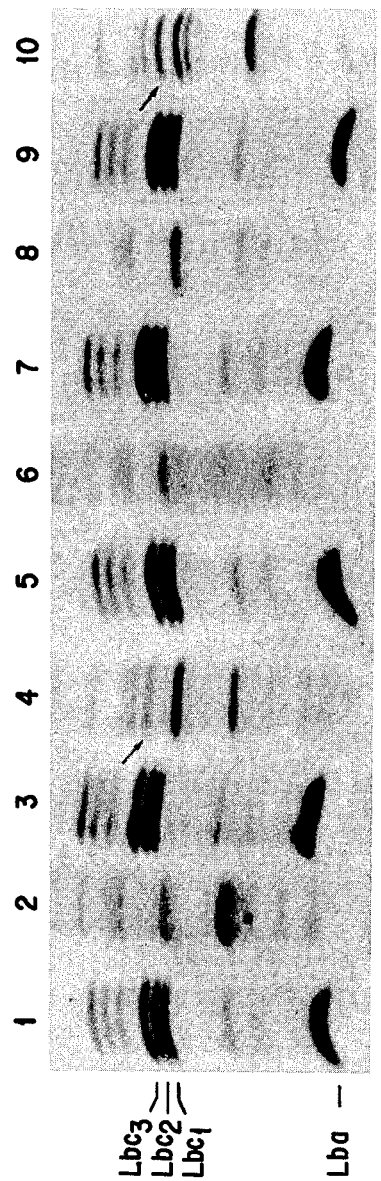
FIG. 14 corresponds to Example 9 and shows a demonstration of Lb$_3$ protein in bird's-foot trefoil plants transformed with the soybean Lbc$_3$ gene.

(see FIG. 14)

Proteins extracted from root nodules of $Lbc_3$ transformed (L8-35), $Lbc_3$ 5' 3'-CAT-transformed and non-transformed plants were separated by isolectric focusing at a pH gradient of 4 to 5. The columns 1, 3, 5, 7, and 9 show $Lbc_1$, $Lbc_2$, $Lbc_3$, and Lba proteins synthesized in soybean control root nodules. Column 2 shows proteins from root nodules of $Lbc_3$-5'-3'-CAT-transformed L-6-23-bird's-foot trefoil plants, whereas the columns 6 and 8 show proteins from nontransformed plants. The columns 4 and 10 show soybean $Lbc_3$ protein synthesized in root nodules of bird's-foot trefoil plants (L8-35) transformed with the $Lbc_3$ gene. The $Lbc_3$ protein band is indicated by an arrow.

In connection with the invention it has thus been proved that root nodule-specific genes can be expressed tissue-specifically upon transfer to other plants, here *Lotus corniculatus*. It has furthermore been proved that expression proved above allows production of an active, functional, nitrogen-fixing root nodule on this plant upon infection by Rhizobium. In this manner these plants can grow without the supply of nitrogen. Root nodule-specific promoters, here exemplified by the $Lbc_3$ promoter, must be used in the present case for regulating the expression of the transformed genes.

By the above use a root nodule-specific promoter is used for expressing genes, the gene product or function of the gene product of which improves the function of the root nodule, e.g. by altering the oxygen transport, the metabolism, the nitrogen fixation or the nitrogen absorption.

By the above use root nodules are used for the synthesis of biological products improving the plant per se or which can be extracted from the plant later on. A root nodule-specific promoter can be used for expressing a gene, the gene product or compound formed by said gene product of which constitute the desired product(s).

In connection with the present invention it has furthermore been proved that the soybean $Lbc_3$ leghemoglobin protein per se, i.e. the $Lbc_3$ gene product, is present in a high concentration in root nodules of bird's-foot trefoil plants expressing the $Lbc_3$ code sequence under the control of the $Lbc_3$ promoter. The latter has been proved by cloning the genomic $Lbc_3$ gene of the soybean into the integration vector pAR1, said genomic $Lbc_3$ gene containing the coding sequence, the intervening sequences, and the 5' and 3' flanking sequences. A 3.6 Kb BamHI fragment $Lbc_3$HH, cf. Example 2, was cloned into the pAR1 plasmid and transferred to bird's-foot trefoil as stated previously.

The high level of Lbc$_3$ protein, cf. Example 9, found in transformed root nodules of bird's-foot trefoil and corresponding to the level in soybean root nodules proves an efficient transcription of the Lbc$_3$ promoter and an efficient processing and translation of Lbc$_3$mRNA in bird's-foot trefoil.

The high level of the CAT activity present in transformed root nodules is also a result of an efficient translation of mRNA formed from the chimeric Lbc$_3$ gene. The leader sequence on the Lbc$_3$ gene is decisive for the translation initiation and must determine the final translation efficiency. This efficiency is of importance for an efficient synthesis of gene products in plants or plant cells. An Lbc$_3$ or another leghemoglobin leader sequence can thus be used for increasing the final expression level of a predetermined plant promoter. The construction of a DNA fragment comprising a Lb leader sequence as first sequence and an arbitrary promoter as second sequence is a particular use of the invention when the construction is transferred and expressed in plants.

We claim:

1. A method of expressing an exogenous gene in a leguminous plant part, which comprises transforming said leguminous plant part with a first DNA fragment which comprises a 5' flanking region of a leghemoglobin gene obtained from a different leguminous plant species, said 5' flanking region being an inducible promoter of said leghemoglobin gene, and a second DNA fragment which encodes the exogenous gene to be expressed, wherein said first DNA fragment is positioned 5' to said second DNA fragment so that said first DNA fragment regulates expression of said exogenous gene.

2. A method according to claim 1, wherein said 5' flanking region is a 5' flanking region of a soybean leghemoglobin gene.

3. A method according to claim 1, wherein said 5' flanking region is obtained from the Lba gene and has the following sequence:

```
GAGATACATT ATAATAATCT CTCTAGTGTC TATTTATTAT TTTATCTGGT
GATATATACC TTCTCGTATA CTGTTATTTT TTCAATCTTG TAGATTTACT
TCTTTTATTT TTATAAAAAA GACTTTATTT TTTTAAAAAA AATAAAGTGA
ATTTTGAAAA CATGCTCTTT GACAATTTTC TGTTTCCTTT TTCATCATTG
GGTTAAATCT CATAGTGCCT CTATTCAATA ATTTGGGCTC AATTTAATTA
GTAGAGTCTA CATAAAATTT ACCTTAATAG TAGAGAATAG AGAGTCCTGG
AAAGTTGGTT TTTCTCGAGG AAGAAAGGAA ATGTTAAAAA CTGTGATATT
TTTTTTTTGG ATTAATAGTT ATGTTTATAT GAAAACTGAA AATAAATAAA
CTAACCATAT TAAATTTAGA ACAACACTTC AATTATTTTT TTAATTTGAT
TAATTAAAAA ATTATTTGAT TAAATTTTTT AAAAGATCGT TGTTTCTTCT
TCATCATGCT GATTGACACC CTCCACAAGC CAAGAGAAAC ACATAAGCTT
TGGTTTTCTC ACTCTCCAAG CCCTCTATAT AAACAAATAT TGGAGTGAAG
TTGTTGCATA ACTTGCATCG AACAATTAAT AGAAATAACA GAAAATTAAA
AAAGAAATAT G.
```

4. A method according to claim 1, wherein said 5' flanking region is obtained from the Lbc$_1$ gene and has the following sequence:

```
TTCTCTTAAT ACAATGGAGT TTTTGTTGAA CATACATACA TTTAAAAAAA
AATCTCTAGT GTCTATTTAC CCGGTGAGAA GCCTTCTCGT GTTTTACACA
CTTTAATATT ATTATATCCT CAACCCCACA AAAAAGAATA CTGTTATATC
TTTCCAAACC TGTAGATTTA TTTATTTATT TATTTATTTT TACAAAGGAG
ACTTCAGAAA AGTAATTACA TAAAGATAGT GAACATCATT TTATTTATTA
TAATAAACTT TAAAATCAAA CTTTTTTATA TTTTTTGTTA CCCTTTTCAT
TATTGGGTGA AATCTCATAG TGAAGCCATT AAATAATTTG GGCTCAAGTT
TTATTAGTAA AGTCTGCATG AAATTTAACT TAACAATAGA GAGAGTTTTC
GAAAGGGAGC GAATGTTAAA AAGTGTGATA TTATATTTTA TTTCGATTAA
TAATTATGTT TACATGAAAA CATACAAAAA AATACTTTTA AATTCAGAAT
AATACTTAAA ATATTTATTT GCTTAATTGA TTAACTGAAA ATTATTTGAT
TAGGATTTTG AAAAGATCAT TGGCTCTTCG TCATGCCGAT TGACACCCTC
CACAAGCCAA GAGAAACTTA AGTTGTAAAC TTTCTCACTC CAAGCCTTCT
ATATAAACAT GTATTGGATG TGAAGTTATT GCATAACTTG CATTGAACAA
TAGAAAATAA CAAAAAAAAG TAAAAAAGTA GAAAAGAAAT ATG.
```

5. A method according to claim 1, wherein said 5' flanking region is obtained from the Lbc$_2$ gene and has the following sequence:

```
TCGAGTTTTT ACTGAACATA CATTTATTAA AAAAAACTCT CTAGTGTCCA
TTTATTCGGC GAGAAGCCTT CTCGTGCTTT ACACACTTTA ATATTATTAT
ATCCCCACCC CCACCAAAAA AAAAAAAACT GTTATATCTT TCCAGTACAT
TTATTTCTTA TTTTTACAAA GGAAACTTCA CGAAAGTAAT TACAAAAAAG
ATAGTGAACA TCATTTTTTT AGTTAAGATG AATTTTAAAA TCACACTTTT
TTATATTTTT TTGTTACCCT TTTCATTATT GGGTGAAATC TCATAGTGAA
ACTATTAAAT AGTTTGGGCT CAAGTTTTAT TAGTAAAGTC TGCATGAAAT
TTAACTTAAT AATAGAGAGA GTTTTGGAAA GGTAACGAAT GTTAGAAAGT
GTGATATTAT TATAGTTTTA TTTAGATTAA TAATTATGTT TACATGAAAA
TTGACAATTT ATTTTTAAAA TTCAGAGTAA TACTTAAATT ACTTATTTAC
TTTAAGATTT TGAAAAGATC ATTTGGCTCT TCATCATGCC GATTGACACC
CTCCACAAGC CAAGAGAAAC TTAAGTTGTA ATTTTTCTAA CTCCAAGCCT
TCTATATAAA CACGTATTGG ATGTGAAGTT GTTGCATAAC TTGCATTGAA
CAATAGAAAT AACAACAAAG AAAATAAGTG AAAAAAGAAA TATG.
```

6. A method according to claim 1, wherein said 5' flanking region is obtained from the Lbc$_3$ gene and has the following sequence:

```
TATGAAGATT AAAAAATACA CTCATATATA TGCCATAAGA ACCAACAAAA
GTACTATTTA AGAAAAGAAA AAAAAAACCT GCTACATAAT TTCCAATCTT
GTAGATTTAT TTCTTTTATT TTTATAAAGG AGAGTTAAAA AAATTACAAA
ATAAAAATAG TGAACATCGT CTAAGCATTT TTATATAAGA TGAATTTTAA
AAATATAATT TTTTTGTCTA AATCGTATGT ATCTTGTCTT AGAGCCATTT
TTGTTTAAAT TGGATAAGAT CACACTATAA AGTTCTTCCT CCGAGTTTGA
TATAAAAAAA ATTGTTTCCC TTTTGATTAT TGGATAAAAT CTCGTAGTGA
CATTATATTA AAAAAATTAG GGCTCAATTT TTATTAGTAT AGTTTGCATA
AATTTTAACT TAAAAATAGA GAAAATCTGG AAAAGGGACT GTTAAAAAGT
GTGATATTAG AAATTTGTCG GATATATTAA TATTTTATTT TATATGGAAA
CTAAAAAAAT ATATATTAAA ATTTTAAATT CAGAATAATA CTTAAATTAT
TTATTTACTG AAAATGAGTT GATTTAAGTT TTTGAAAAGA TGATTGTCTC
TTCACCATAC CAATTGATCA CCCTCCTCCA ACAAGCCAAG AGAGACATAA
GTTTTATTAG TTATTCTGAT CACTCTTCAA GCCTTCTATA TAAATAAGTA
TTGGATGTGA AGTTGTTGCA TAACTTGCAT TGAACAATTA ATAGAAATAA
CAGAAAAGTA GAAAAGAAAT ATG.
```

7. A method according to claim 1, wherein said leguminous plant part is further transformed with a third DNA fragment which comprises a 3' flanking region of a leghemoglobin gene obtained from a different leguminous plant species, wherein said third DNA fragment is positioned 3' to said second DNA fragment.

8. A method according to claim 7, wherein said 3' flanking region is of a soybean leghemoglobin gene.

9. A method according to claim 7, wherein the 3' flanking region is of the Lba, $Lbc_1$, $Lbc_2$ or $Lbc_3$ gene with the following sequences respectively:

Lba with the sequence:

```
                1590                                              1620
      TAA TTA GTA TCT ATT GCA GTA AAG TGT AAT AAA TAA ATC TTG
                1650                                              1680
  TTT CAC TAT AAA ACT TGT TAC TAT TAG ACA AGG GCC TGA TAC AAA ATG TTG GTT AAA ATA
                1710                                              1740
  ATG GAA TTA TAT AGT ATT GGA TAA AAA TCT TAA GGT TAA TAT TCT ATA TTT GCG TAG GTT
                1770                                              1800
  TAT GCT TGT GAA TCA TTA TCG GTA TTT TTT TTC CTT TCT GAT AAT TAA TCG GTA AAT TA
                1830                                              1860
  ACA AAT AAG TTC AAA ATG ATT TAT ATG TTT CAA AAT TAT TTT AAC AGC AGG TAA AAT GTT
      ATT TGG TAC GAA AGC TAA TTC GTC GA
```

$Lbc_1$ with the sequence:

```
                                                            * 1320
                              TAA/TT AGG ATC TAC TGC ATT GCC GTA
                1350                                              1380
      AAG TGT AAT AAA TAA ATC TTG TTT CAA CTA AAA CTT GTT ATT AAA CAA GTT CCC TAT ATA
                1410                                              1440
      AAT GTT GTT TAA AAT AAG TAA ATT TCA TTG TAT TGG ATA AAC ACT TTT AAG TTA TAT ATT
                1470                                              1500
      TCC ATA TAT TTA CGT TTG TGA ATC ATA ATC GAT ACT TTA TAA AAA TAA ATT CCA AAT AAT
      TTA TAC GTT TTA AAA ATT ATT TT
```

$Lbc_2$ with the sequence:

```
                                    TAG/GAT CTA CTA TTG CCG TCA AGT
                                                                1140
      GTA ATA AAT AAA TTT TGT TTC ACT AAA ACT TGT TAT TAA ACA AGT CCC CGA TAT ATA AAT
                                  1170                              1200
      GTT GGT TAA AAT AAG TAA ATT ATA CGG TAT TGA TAA ACA ATC TTA AGT TTT ATA TAT AGT
                                  1230                              1260
      TCC ATA TAC TAA AGT TTG TGA ATC ATA ATC GA
                                  1290
``` and $Lbc_3$ with the sequence:

```
                              TAG/GAT CTA CAA TTG CCT TAA AGT GTA ATA AAT AAA
                            *   990                                              1020
```

-continued

TAT TAT TTC ACT AAA ACT TGT TAT TAA ACC AAG TTC TCG ATA TAA ATG TTG GTT AAA CTA
                              1050                                              1080

AGT AAA TTA TAT GGT ATT GGA TAA ACA ATC TTA AGC TT.
                    1110

* * * * *

UNITED STATES PATENT AND TRADEMARK OFFICE
CERTIFICATE OF CORRECTION

PATENT NO. : 4,886,753

DATED : December 12, 1989

INVENTOR(S) : KJELD A. MARCKER, ET AL.

It is certified that error appears in the above-identified patent and that said Letters Patent is hereby corrected as shown below:

ON THE TITLE PAGE:

item [54], last line after "Plants" delete "," .

Signed and Sealed this

Ninth Day of April, 1991

*Attest:*

HARRY F. MANBECK, JR.

*Attesting Officer*      *Commissioner of Patents and Trademarks*